US009657277B2

(12) United States Patent
Shin et al.

(10) Patent No.: US 9,657,277 B2
(45) Date of Patent: May 23, 2017

(54) BACTERIOPHAGE AND ANTIBACTERIAL COMPOSITION COMPRISING THE SAME

(71) Applicant: CJ CHEILJEDANG CORPORATION, Seoul (KR)

(72) Inventors: Eun Mi Shin, Seoul (KR); Gi Duk Bae, Seoul (KR); Jae Won Kim, Yongin-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/770,429

(22) PCT Filed: Feb. 24, 2014

(86) PCT No.: PCT/KR2014/001477
§ 371 (c)(1),
(2) Date: Aug. 25, 2015

(87) PCT Pub. No.: WO2014/133290
PCT Pub. Date: Sep. 4, 2014

(65) Prior Publication Data
US 2016/0083697 A1    Mar. 24, 2016

(30) Foreign Application Priority Data

Feb. 27, 2013   (KR) ........................ 10-2013-0021497

(51) Int. Cl.
| | |
|---|---|
| *C12N 7/00* | (2006.01) |
| *A61K 35/76* | (2015.01) |
| *A01N 63/00* | (2006.01) |
| *A23L 3/3463* | (2006.01) |
| *A23L 2/44* | (2006.01) |
| *A23K 10/18* | (2016.01) |
| *A23K 20/195* | (2016.01) |
| *A23K 50/30* | (2016.01) |

(52) U.S. Cl.
CPC ............... *C12N 7/00* (2013.01); *A01N 63/00* (2013.01); *A23K 10/18* (2016.05); *A23K 20/195* (2016.05); *A23K 50/30* (2016.05); *A23L 2/44* (2013.01); *A23L 3/3463* (2013.01); *A61K 35/76* (2013.01); *C12N 2795/10221* (2013.01); *C12N 2795/10231* (2013.01); *C12N 2795/10233* (2013.01)

(58) Field of Classification Search
None
See application file for complete search history.

(56) References Cited

U.S. PATENT DOCUMENTS

| 6,485,902 B2 | 11/2002 | Waddell et al. | |
|---|---|---|---|
| 2016/0083696 A1* | 3/2016 | Shin .................. | C12N 7/00 424/93.6 |

FOREIGN PATENT DOCUMENTS

| CN | 101724607 A | 6/2010 |
|---|---|---|
| KR | 10-2009-0021475 A | 3/2009 |
| KR | 10-2009-0030532 A | 3/2009 |
| KR | 10-0910961 B1 | 8/2009 |
| KR | 10-2009-0128239 A | 12/2009 |
| KR | 10-2010-0116289 A | 11/2010 |
| KR | 10-2011-0041670 A | 4/2011 |
| WO | 2004/020406 A2 | 3/2004 |

OTHER PUBLICATIONS

Wang et al. Isolation and Characterization of a Lytic Bacteriophage of Enterotoxigenic *E. coli* K88. ACTA Agriculturae Boreali-Sinica: 2012, 27 (4): 163-167.*
Kim et al., "Evaluation of bacteriophages for prevention and treatment of diarrhea due to experimental enterotoxigenic *Escherichia coli* K88 infection of weaned piglets", Korean J. Ver. Serv., 2011, vol. 34, No. 4, pp. 341-252.
Jamalludeen et al., "Isolation and characterization of nine bacteriophages that lyse O149 enterotoxigenic *Escherichia coli*", Veterinary Microbiology, 2007, vol. 124, pp. 47-57.
Jamalludeen et al., "Evaluation of bacteriophages for prevention and treatment of diarrhea due to experimental enterotoxigenic *Escherichia coli* O149 infection of pigs", Veterinary Microbiology, 2009, vol. 136, pp. 135-141.
International Search Report dated Apr. 28, 2014 of PCT/KR2014/001477 which is the parent application—5 pages.
Dai, "Isolation, Identification and Biological Properties of the Bactenophages for *E. Coli* K88", China Master's Thesis Full-text Database Agricultural Science and Technology, Dec. 15, 2009, pp. D050-110.
Dai, Bao-Ying, "Isolation and classification of *Escherichia coli* bacteriophage, and determination of its biological characteristics," Chinese Master's Theses Full-text Database—Agriculture Science and Technology, Dec. 15, 2009, issue 12.
Office Action dated Oct. 14, 2016 of corresponding Chinese Patent Application No. 201480010869.2—7 pages.
Cha et al., "Effect of Bacteriophage in Enterotoxigenic *Escherichia coli* (ETEC) Infected Pigs", Journal of Veterinary Medical Science, vol. 74, No. 8, pp. 1037-1039, 2012.
Wietzorrek et al., "The Genome of the Novel Phage Rtp, with a Rosette-Like Tail Tip, Is Homologous to the Genome of Phage T1", Journal of Bacteriology, vol. 188, No. 4, pp. 1419-1436, 2006.
Yoo et al., "Field evaluation of Enterotoxigenic *Escherichia coli*-specific bacteriophage (CJ19) as a feed additive", Korean J Vet Res, 2013, vol. 53, No. 2, pp. 83-88.

(Continued)

*Primary Examiner* — Michelle S Horning
(74) *Attorney, Agent, or Firm* — Knobbe Martens Olson & Bear LLP

(57) ABSTRACT

Provided is a novel bacteriophage ΦCJ19 (KCCM11361P). In addition, the present invention relates to an antibacterial composition including the bacteriophage ΦCJ19 (KCCM11361P) as an active ingredient. Further, the present invention is a method of preventing and/or treating infectious diseases by enterotoxigenic *Escherichia coli* in animals except for humans using the bacteriophage ΦCJ19 (KCCM11361P) or the antibacterial composition containing the bacteriophage ΦCJ19 (KCCM11361P) as an active ingredient.

10 Claims, 3 Drawing Sheets

(56) References Cited

OTHER PUBLICATIONS

Extended European Search Report dated Aug. 22, 2016 of corresponding European Patent Application No. 14756265.6—7 pages.
English Abstract of CISLO M, et al., "Archivum Immunologiae et Therapiae Experimentalis", Ther. Exp. 2:175-183, 1987.
Sung Hoon Kim et al., "Bacteriophage, New Alternative Antibiotics", BioWave; Biological Research Information Center, BRIC, 2005, vol. 7, No. 15—10 pages.
Mason, "Transgenic plants as vaccine production systems", Trends in Biotech, 1995, vol. 13, pp. 388-392.
Hong, "The Additive Effect of Egg Yolk Antibody in Early Weaned Pigs", Master's Thesis, Dankook University, 2001—66 pages.

\* cited by examiner

SEQUENCE LISTING

```
<160> NUMBER OF SEQ ID NOS: 1

<210> SEQ ID NO 1
<211> LENGTH: 49619
<212> TYPE: DNA
<213> ORGANISM: Artificial Sequence
<220> FEATURE:
<223> OTHER INFORMATION: a part of DNA of  novel bacteriophage CJ19

<400> SEQUENCE: 1
aagacccaat gaacatgagc atcgagattc cagaatcttt caacatgctc ccgatgcagg        60
cgaaggattt gcactttaag gttccgtgca cctccaagac cactggtctg atcgtatatc       120
gtccgctgac gattatcatg cttgttggcc tgaaagctac cgcttaacac taagcccctg       180
attaacgtca ggggcttttt ttattgacat gcaacattaa aacaattaca ttgaacgtct       240
aggcaataca ctcgttaaac taatcaaaag gaaataaaca tggctaagaa aaacgtcatt       300
aagaacatcg gcgcttgtct ggttcgtatc gaaaagcaag acctgaaacc tgacgacact       360
ctggaggtga cggaagaaca aatcaaatct caggcgttta aatatctttt cttacgcaaa       420
gacattgaat ttgacgatga tccgaagcgc acgcgtgagt acatcgccga aatcaaaaag       480
tccgcgaagg ttaagccgga aaaagaagtg aaagatattg aagatcttga aactggcaag       540
gaatacaaat aacctatagg ggcgctgatg cgtcccttt ttttaacatg aggaagctac       600
tatgaatgaa gatcagatta aggcgttcga gtttatgtgc cagttggcac cagcattacg       660
aaaggttgat agcgtcacct ttctggcttg gatggtgctg gctgaatcgt tcgtgtgcaa       720
gaataaattc ggtgctgact attacaaagc actggccctg tacaccatgc acttgatgtt       780
tttggatggt gcaatgaagg gcgagaatga aagtcttgag aactactcac gtcgagtaac       840
gtcattctcc ctgagcggtg aattttcgac tggctacgga tctgtaactc agaacactga       900
tgggcgtcag attacacaaa ccccatgggg caaaatgtac gacgttatca acaagaagaa       960
aggcggcggc ttcggcatga tctctggtat tcgggcgcgg gggtgtgtgc gatgattgat      1020
tataacgaag tccaaaggct taccgatcag gggattaatg ccttctctgg aaacgatgag      1080
atcggcttcg acatcatcat cactggcgga ggcgttcaga tgattgatgg cgaggaagtt      1140
```

```
aaggctcctg aagttcgcgg gaaagttttc ggcgctgttc gtgctatcag ttaccacatg   1200
attgatggtg aatctatcaa gctgggtgat aagcgcgctt tcttctctaa cgttacacca   1260
attgaaaacg ggatggttat catccttgat ggccagcact ggcgcgtcgt ggatagtcga   1320
ccagttaacc caactcaatc tcacgttatc gcttatcgtc cgatacttcg caaggtggcg   1380
acgcatggct aactacatcg tcaggaagtt ccagggcgat atagagaagt ggattaagca   1440
ggttaaatcc ggccttgatg acgtaattcg tgagttcgtc aaggctgttc acgctgattt   1500
agttaaagga tcaccagttg atactggtcg tttcagagct aactggcaga taacctacaa   1560
ccacataccg atgtacgcac tgaatgagta cgataaatca ggtagtaaaa ccattgcgtc   1620
aggtataagg acggctaacg cattaccgtt aggccgtggc ggcgcggtga ctaccatata   1680
cttttccaac atgctgatat acgccaacgc tcttgagtat ggtcattcac aacaagcgcc   1740
agctggcgta cttggcctgg tggctgttcg gttgagaact tacatggctg aagcaattat   1800
tgaatcaagg agcaaaaatg gtttatgacg attacgacct ggcggtcgcg gcgcgtaagg   1860
cgctatcatc tgagttcggc ggtcggtttc cgatcatgtt tgagaacgtg ccattcaaag   1920
agcctgacga tggctcaacg tggctaaagt tcgattacat tcctgctgag aaaacttaca   1980
aatcattgag ccgtaagtgt atcaggattc gtggccttgt ccaaattggc attgtttttct   2040 cgcctgatac tggcatggat gacgcgcgca aactagcaaa agaaattgct aatttcttcg   2100
aagatggtaa aatccttttct gtaggttttta ttttttgaagg cgcgagccaa aagcccgtgc   2160
agaaatcaca acgaggctgg ttaattccaa tccgcttcac agtacaacac gacgaataaa   2220
ggagcattaa ctatggcact tcctaacggt tcccaaatct ttattgagca gaccagagca   2280
gccatcgaaa tcgaagcaac cgcagtgagt aacgcggaaa atccggtggc gactgttgcg   2340
tcaaccactg gcattgtgaa aggcgattac gtcctggtgc tggaaagcgt atgggctgca   2400
tttaaaaatc gcgtaatgcg agtgaaagaa gtaaccctgg acgcatcaat cacgcttgaa   2460
ggcgacaaga acacttccac ggctgacctt aacaagttcc ccgctggcgg cgcttccacc   2520
ttcgttaaga tcgaaagctg gattgagatt ccatgcgtga gcgacattgc aaaatctggc   2580
ggagagcagc agttctatac caagcagtgt ctttcagatg accgagagaa gcagatcccg   2640
acctttaaat ctgcgacgtc catcgcgtat acgttcgact tcgactactc caacccaatc   2700
actcagcttc tgattggtta cgacgaagac ggcaagacgc gagctatgcg aatgttcgta   2760
ccgaaggcaa gctatccgat ccgcaccttc tctggtactc catctttcga tgacatccct   2820
aacacggtga tgaacgaaga tgaaacgacc atcctgacca tctcacttga tggtaaaatat   2880 actcacatga aagagtttgt ggtgtaaatc gaggggggcta ttgcccccctc tttttatttg   2940 tggtttaata gatactcaat taacgagagg gcatttcaaa tggctgcaaa atttaaagta   3000
actttgggcg cactgcctga tttcattctt ccggtttctt tcgtcatgcc aaacggagat   3060
gaggctgaga ttaaattcaa ggttcgccac aagaaagcaa gcgaaatcaa agcgctatat   3120
gacggcgagg cgaaggatta tacctttatc aacgaggttt gcactggctg ggatctggag   3180
gatgagttta attccgaaaa cgcacaggcg attgttgatc tcttcccatc cattgcactg   3240
gcgctggctc aagcctacat gggcgccctc gttggtcagc gagtaaaaaa ctaaaaaggg   3300
cgatccggtt gatgttccaa aaatcaccga ctgatgcaga gcttgaagcg tacggattga   3360
cccgtgaaga ttcgaggat gaagagcctg agatattaat cttttgatgag tcaatgtatc   3420 agtcatggga gatattcaac gcaatgaata ctcagtggag atcatccgga ggcgtccctt   3480
```

```
acggtcttga ttataatgtg ttgccgatgt tgttcagaat ctataaaata gacgatgagg    3540
aaatggcact caatgatgtg cgagtaatgg agggcttatc cctacaactc atgcacaaaa    3600
agtaataagc gcctacgggc gctttttttg tttgggggtt ttatgacaga taaatttgca    3660
gggctatccc ttggtgttga cgtttcccag gttgataagg cggtgaaatc actggagaac    3720
ttctccaagg ctaacaataa ggcgactggc tctctctctg attttgtcga taatgaacag    3780
gtggcaagga cgaaggcaaa agagcttgcg gctgaattgg cacgccagcg tgccgagttc    3840
cagaagcttg agggagtcat tgacccgaca gctagcaaaa tggcacgact taaaactgct    3900
agtgagcaac ttgatgcggc gtggcaaaag ggagttgtac ctgataaaaa gttttcgaa     3960 ttaggtgaaa tgcttgaggc gcagaataac gcgctaatca agtcacgctc tatattgaca    4020
gcagaggggc gtgctgcggc ggaaaattcc aagcagaaag ccagagccaa agctgatgcc    4080
gatagcttca ttcgaagcct tgagcgtcaa gctcaagcgg ctacgatgac gaagcaagaa    4140
atgcttgagc ttagggcggc tgagttgggc gtatcggaca aagcgtctcc tttgatttct    4200
aagttaaatc agcaaacgga agcattcaaa ctcagcggaa tctcagcggg tcaataccga    4260
aacgcaatga agatgctacc tgcgcagatt actgatgttg taacatcaat ggcgactggg    4320
atgccgatat ggatggttgc catccagcag ggcggacaga tcagcgattc attcggcgga    4380
attggtaacg cgatgcagtt agcgaaggat ggcgtgattg attatatatc atccattaca    4440
gagcttaaat cagcattcgc agatgtaaga accttgggtc aagatgcgat taccagattc    4500
ggacgtgcga caacgatttt cggcggcggc attgtcacgg cggttgctgc tattggttat    4560
gcggcttact cctcatactc tgagctgagt gagcttcaaa gcgctatcgt tctgagcggt    4620
ggatatgctg ttcaatcagc ggccgaaatg gatacattga ccgatgcgat caccgaaaac    4680
agcaaggcaa gcggaggggc ggttaaggac atcgctgcat ctatggctaa gtctggcaag    4740
tacacatccg atcaaatcaa aatcatcacc gcatccacgg cagattgggc gacagtaaca    4800
agcacaagcg cagataagat ccttgcggag ttcgataaga ttgcaaaaga tccgttagc     4860 ggactgatag agttaaacaa gacatataac ttcctagaga aaggccagtt aacatacatc    4920
aacaagctta agaaaacgga aggtcaaact gcggcggtta ctgctgcgac gaaaatttc     4980 gccgatgtaa tggatgatcg aattgcaaag cttgcggaat cagcaaaccc actagagaaa    5040
atgtggtgga atatcaagaa atggtctagc gacgcgtggg gttccgtttc cgacaggacg    5100
ctaggggcgc taaatctgat caccgatgta gttgctggca cggttgagca ggtcaaggtg    5160
atcctcaact atggagatca gtacattggt gagttcgtca tttcagctac aaaggcgatg    5220
caagggattc ctggcatggg cactttcggt caatcggtga tcgacgagca gcagaaaatt    5280
gttgacgcag ccaaaaaaca aaacgaggag ttgttaaaat ccatcgcaga gcgcgatgcc    5340
aggatcagaa aagggggaaac tggatacctt gaagcgggaa agaatgataa ggtaggagac    5400
ggttattcat caaaaacaaa agaagctgta gacaaagagg cagaggctct aaaaaaatta    5460
aacaaggaaa agaaatactc agtcgaacag ggtattaaaa tcaccgatca gtacgaaatg    5520
gatattgtcg ccttgcagtc tcagctaaaa gtactgcagg agcataagac catcaacgac    5580
agcatcagcc agcagcgcaa aacgcaatgg aacgagcaag ctcggatact gattctggag    5640
ggtatcgcgg cggatcagaa agggagagcg ctgacgcagg aagagaaatc aatcctttta    5700
aacaaggcca agattctaga ccttgcggaa cagaaagcgg tgttggggga tcagattgtt    5760
gtccaagagc gtttgaataa gttgcaggac gattcagaga agttcgtgaa taagacgctg    5820
gcggcaacaa gatcgctcaa cgataccaaa gcgatgggcg acagggaggc aaaacgctac    5880
```

```
gctgaaagag aggctatgaa agccgattgg gcgaacaggg gcgggaaaga tgctgatccg    5940
gcactaaaaa gaatgcttga tgagcaagat aagtactacg cggcgaaaga tgcgaagcgt    6000
gctgactggt tggctggggc tgaaaacgct tttgaaaact acggcgcagc ggcaacggat    6060
atgtatacca acgttggcag tatcgcaacg agcgcattaa acggaatgtc tgacatgatg    6120
actgagtttt tgatgacggg gcaggccaac ttcgctgact tcgcaaagag cattatcagc    6180
cagatcatta agatgatcac gcagatggta atcttcaact caatctccgg catgatgggc    6240
ggctcggctg gtggtaaggg attctccttc gctaactcag gatggttcgc tactggcggg    6300
tacaccggag acgtgggaa atatgagcct gctggaacag tacacaaggg tgagttcgtc    6360
atgaccaagg aagcgacaaa gcgaattggc gtagataacc tttatcgaat gatgcgaggt    6420
tatgcgaatg gagggatggt tggcggaacg tcaagcggtg gcgttggcgg cgcaatcatg    6480
gctggcggcg tgacaattgg tagcatccct gttagcatca ataacggtag cgatccgaag    6540
ggtatggagc aaggcgtgaa aatgattttc aagcaaatga ttcaggaatc atgctcacag    6600
ggtggcgaag tttacaatta catcaaagga aaagcaggag cgtaataaat ggccctagac    6660
gttttcaagt ggtgcgtaca ggttcaggat ggtggcggtg taatgaccgt caccaacaat    6720
gacaggcagg tgcagtttgg caacggattc cgccaggttg catcttctgg ctataacact    6780
gagcgacgag agtacgcaat aagctacgtt ggaaaggact ggaaagaagt gcgcgaattt    6840
ttgcgatcgc acagactgaa agcctttgcc tttaccccac cggaggacaa gatcggcgtc    6900
ttcctattga agcctgacac gctgaatact cagccaatcg gtcgaggact tcttgtcgta    6960
aaatgcacca ttgtagaagc cttcacagcg gtgtagaata aagcctccta acgggggctt    7020
ttttattgga ggtaatccca tgacacctaa gtttgagaac gtcttgcagg ggcttttccc    7080
tggcgagatt ataacgctga ttgacgttga cggcacgaag ttcggagcag acgtataccg    7140
gttccacaat gagaacatcc agtttacgcc ggaggagata ctagcagcta cacagccagg    7200
cgggagcctt cagccaaaaa caatcacctt tcagggaaat gaatatggcg cacgcccttt    7260
cggcatctct ggcattgacc taaatggtaa cggcaaggcc ggaaagcctc agctatcttt    7320
gtcaaacctt gatagccgcg tgtcggcgct tatccggtcc tacaacggca tgatgcaggc    7380
caaggtgact atctggataa cctcacgcga aatgctaggc agtacaggca acgttgcggc    7440
tggcgacttc cgaaaatacg tttactacgt tgagcgaccg aactttgtgg atcagaacct    7500
tgcgcgattc gacctgacat caccatacga tatggatggc attatgatcc cgccgcgagt    7560
aactcagagt gtttgctttt gggcgcagcg tggatggtac agaagcggca acggttgcgg    7620
ttacaacgga agcaggatgt tgataaaga caataatcca gtatcagatc catctcagga    7680
cgtctgtgcg ggaactgtaa cggcctgcaa actgagattc ggagctgaaa acgaattaga    7740
tttcggcggc tgtgcggtcg catcacttga caggaaaaac caatgattaa cggtaaaatc    7800
aagatggcaa tcttcgaaca tgcgaaatca gtatacccaa atgaatgttg cggagtggta    7860
actcaaaagg ggcgggttca aaaatactgg ccaattgaca acgttcactc tgaaccggaa    7920
aaaggattcc agcttgactc tgtgcaatac gcctgcattg aggataacgc cgacctaacc    7980
acgatcgcca ttgttcatag ccataccgga gacggagcga ctacattacc aagcgctcac    8040
gacctgtgcg tattgaacga gatggagtta ccctgggtga ttgtaagcct gccggaaggt    8100
gacatgagaa ttgttcatcc tgaagccatg cctctgattg gtcgcccttg gtcgcttggc    8160
tcttttgatt gctggggtct ggttatggca tggcacaagg agcacggcgt aatactgaat    8220
```

-continued

```
gacttcagaa agccttacga gtggtggaaa cctgagtatg gtgaaaatct ataccaggac    8280
aactacatca aggagggttt tgttgaaacc ggaaaagatc ctgagcctgg tgatatgatc    8340
atcatgaaat tacaagctga ggtgtggaat catgctggga tttaccttgg caataatcaa    8400
cttctacatc acgcatttgg caaactgtca aagacagacg tctattcagg atggttccag    8460
gaacatacgg taatggtttg caaacataag gagttagaaa aatgttaaag acaatcaagc    8520
tatcaggatc gctggggcgc aggttcggcg ttttccacaa atatgatgtt gactcatacc    8580
cggaagcgat tcgggcgtta tcatcccagg tggaagggtt taaggagttc atgcagagtg    8640
agatcggctc acgtatgcac ttcgcagtat tcgttgacgg aaagaatgta ggccagcatg    8700
acgaggcggc attcgtttgt gctaaagagg tccgcattat tccgatccct actggatcaa    8760
aaaacggcgg gatgttccag attgttgttg gtgctgtgat gatggtcgca gcattctaca    8820
ctggcggcgc atcactggcg ctaatgggta cgttcgcaac gtcagcattt atgatgggcg    8880
gcgcaatggt gctaggtggg gtaatgcaga tgatttcacc acagcaaggc ggctcaaaga    8940
tggaggttca aagcagcaag aacaaaccat catacgcctt cggcggcgca gtaaacacga    9000
cagcagcagg aaacccgatc cccgtgccat acgggtatcg aacggtaggc ggagcaacgt    9060
tctcagccta cagcgttgcg gaagatatgg cataagtaaa acccgccttg cgcgggtttt    9120
tttgtgcctg tataatgaaa cttcgataaa tcgcacgaaa ggctaaacat catgattaaa    9180
aatagtgtag tgacgggccg aaagggtggc agcagcaagc cgcatacccc acaggagatg    9240
gaagataacc tgatctcaat caacaagatt aaggttttgc tcgctgttag tgatggcgag    9300
gttgacgcga atttctcatt aaaggactta tatcttaatg acgttcctgt aattgcacca    9360
tccggcgagg ttaactatga aggcgtaacg gctgagtttc gccctggaac gcagactcag    9420
gattacatca aaggcttcaa cgacacggcg gctgagttca ctgtaggccg tgaattgaaa    9480
acaacgacgc cttacgtgat ctcggtaacg aataaacagc tatcagccgt ccgcgtaaaa    9540
atcctgatgc ctcgcggcgt tacaacgaaa gaaaacggcg atatggtcgg cgtggtcgtg    9600
aagtgggccg tagatatggc ggttgatggc gggaactacc aggaagttt  atcagacgtc    9660 atcgacggaa agaccattag cggatatgac aaaacaaagc gaatcgacat cccagcgttc    9720
aatagtcagg ttctattgcg tgtgcgccga gttacggctg attcaactga tgcgcgtgta    9780
gttgacgcga taaacgttca gtcatatgcg gaagtgattg atgctaaatt ccgttaccct    9840
ctgaccggtc ttgtttacgt tgagtttaac agcgagttgt tcccgcagat cccaagtatt    9900
agcacgaaaa agaaatggaa gatcatcaac gttcctagta actacgatcc agtactgaga    9960
gaatatagcg gcacatggga tggtagtttt aaaaaagcat ggtcaaataa tccggcgtgg   10020
gtgctttatg atttgatcac caatcagaga tacggactcg accaaagaga actagggatc   10080
gcggtagata agtggtcact ctatgacgct ggtcaatact gcgatcagaa agtaccagac   10140
ggtcacggcg gaacagagcc tcgctatctt tgcgatgttg tgattcagtc tcaggttgaa   10200
gcgtacaatc tggtgcgaga catttgctca atattccgag gaatgagttt ctggaacgga   10260
gagagccttt caattgtcat cgaccgaccg agagaggcgt cttatatttt cactaacgat   10320
aacgtcgttg atggctcatt tgcctatacg ttcgcaagtg aaaaaagcat gtacacaacc   10380
tgcaacgtca cgttcgacga cgagcagaac atgtacagcc aggacattga gggtgtgttc   10440
gaccttaacg cctcgttacg cttcggtcat aacccgacaa gcatcacagc aatcggatgt   10500
actcgacgca gtgaagcgaa tcgacggggc cgctgggttc tcaaaacaaa ccttcgcagc   10560
acgacggtga gttttgcaac tggccttgag ggtatgattc cgatgattgg cgacgtggtg   10620
```

```
gcaatcgctg ataacttctg gtcaagcaac ctgacgcttt cgttatcagg tcgcgtgatg   10680
gaggtgtctg gcctgcaagt gttcacacac tttaaggtag atgcacgcgc tggtgatttc   10740
attatcgtga acaaggctga tggtaatccg gtgcgccgga ctatttcaaa agtgtctgcg   10800
gacgggaaaa cgattgagct taacgttggg tttggctttg atgttcaacc aaacacagta   10860
ttcgcaatcg accgcactga tgttgccttg cagcaatacg ttgtaaccgg aatcacgaag   10920
ggcgacggcg acgatgagtt cacgtacagc attacggcag ttgaatacga tccgaacaaa   10980
tacgacgaga ttgactacgg cgtaaatatt gatgaccgac caaccagcat tgtagatcct   11040
gacaacatgc agccacctaa aaatatcaag gtgtcttcat attcaagaat tgtccaggga   11100
atgagcgtag aaactatggt catctcatgg gataaagtgc agtacgcgag caagtacgat   11160
gtgcagtggc gcaaggacaa tggcaactgg atgaacgtac cgcgcacagc aaacaaagaa   11220
gtcgaggttg aagggattta cgcaggcaat tatcacgtac gcgtaaggag catctcaagc   11280
ggtggaaata cgtctccatg gtctgaagtt gtcagcgtcg gattgacggg taagattggg   11340
aaaccagata aaccaacagt agtaatagca tctgacgatc aggtgtttgg gattagggtt   11400
aaatggggat tccctgaagg ctctggtgat actgcataca cggagttgca gcagatacca   11460
gataatggtg ctggaggtca cgctggtgag gagaatgcga gtctattaac aatgattcca   11520
tacccacagt acgagtactg gcactcgaca ctgccagcag gatatgtgaa ctggtacaga   11580
gcgagattag tggacagaat tgggaacgta tctgactggt ctgacattgt tcgaggaatg   11640
gctagtgatg acgtggaatc gatcattggt gaaattaagg ttgatatcga gaattccgag   11700
gggtttaagt atctacagca gaacgccatt gagtcaaacg gagctattca ggcgcaagcg   11760
gaatcaattc ttgagaacgc cattgcaaac gacacggatg tgcgtcgaat gactaaggaa   11820
aacggcagga ggaaggctga atatgttcag gcagtgaatc ttattgcaga tgaaactcag   11880
gctcgtgtag aggctctcac gcagcttaaa gcgcagattg atgatgaggt cgtagcctcc   11940
ataactgaag ttcagacggc actagcaacc gaaacggaag ctaggactac tgccgacact   12000
gctttaagcg ctcagcttgg cgacacgcag gccgcactga atgaaaaact tgactcatgg   12060
gtagatgctg aatcagctgg cgctcagtac ggcgttaaat tgggcctcaa atacaatggg   12120
gttgaatata gcgcagggat gagcatggaa cttgttggca gcggtgctgg tgttaagagt   12180
cagttcatat ttgacgctaa cagattcgcg atcagtaatg gggttggttc tggttccggt   12240
cagtgggcat tgccttttgt tgttgagagc aaccaggtgt tcatacagag cgccgtaatc   12300
aaggacggtt caatcacgaa cgctaagatt ggtaacagga tccaatctaa caactacgtt   12360
caaggaagtc atgggtgggc tattgataaa tctggttttg ctgaactaag taatgccacc   12420
gttagaggaa gcctttacgc taacaatggt aacttcgcgt ttaacggaac aagcaacact   12480
gttcagatta acggtaacgg aatcactgtt aacctgccag gtggaggaag ggttgtagtt   12540
ggagtatgga gttaacatat agcccccttc tgggggcttt tttagtacat gtttggtatg   12600
tacggtaacc gcattgatat gttggtgttg aatgggaact gcgcgccaga ctgcgttgag   12660
tagttaccat aaacacttcc tttatgcgcc ctaacctgac catttgacat cgcaacgccc   12720
ttgtatctaa ggttgttgta tccgccagta acctcaacca tcgcgccgca ccttagtatt   12780
gggaaaaacc cattacctat tgattggtat gagttggaaa gctggaggaa tccacttagt   12840
acaaaaggtc gcttgacgct ggaaaacact atctggccag aggcgtttga cattgttaaa   12900
ccaggcccgg cggttggtgc tgtattgttg aatataacaa gatcgatagt tactgatgct   12960
```

-continued

```
gagacattat caattcctgt gtaggtattg tttctacata gtattcttgc cccgtcaaac   13020
tcaagggtga cgtttgggtt attccacctt ccaaacggta ttccagtcac cgggagtgtg   13080
tagcttccat tcacagtcac agttccgaca tactgagcag tcaggagtct actgtttgat   13140
gttattgcag tgaagttagt cgaatcactg acaaatatcc cctcgctgcc tggtgatgca   13200
ccaagaacct caaagccttg cgcgccaaat ccatcaaat gtcctgatga gccgttaaag    13260
ttccctatac ttatccttcc agttgagtta ttgaccctgg aaaatccatt catgaaataa   13320
acctcaggta tgaagtcgaa gtcataaacg tcaatagcct ttgtcggcaa tatgaaggcc   13380
gcagatcctt gagtcattgt tagtccgaag tctctagtgc cattggcgga atcaaacgtg   13440
gagttactgc taaggcttcc tgttactgcg ggcgctctta aacctgcagt tatctccatt   13500
ctcggtcttc cgtcattcaa gtctatcaag ataccctgag gcattatttc cactccttgg   13560
tgccataatc tttaactgat ccagagaggt ttttgatacc atcccagcgg atatctgttt   13620
cacctgaagc tacaactaca cctcctttcc atttagcaac acatgagccg ttaacttcag   13680
tcgcgcacca accgtcaggt cggggtccgg aagaacaacc tacagtcatg attactgctg   13740
ctgcgattat tgccgatttg atgaatttag tcattttgta ttccttagtg agtgtgtttc   13800
gtttcgatgg agtaactata gcaaggatg attacgagt atttagctat tcgtgctatt     13860
gtatacgcgt aaccgatgta actcggtgta tgcaatctcg tccgcggaaa atgatatacg   13920
cgctgttacg ccaatttacg cattagttac attaaaatat ctatatatat caaccttta    13980 ctcttattat tattatatat atattactgt gtatatcatg taactacttc tatagagtgt    14040
tccgcttata aatttctaat atgtacattt atacagtgtt tagtcacacg cacaccaatg   14100
caccatctgt tgaaaatgat atacacgata tacaagctat ttacattgag ctatggctgg   14160
tccggatagc ctttttatgt aactaacacc aatgtataca tcgaattaca gctatatacg   14220
tgtaaccact tgactaatgc gactaagcga gtatagttag ccacatcaac aacgaacgag   14280
gattaaagag atgaccaagc cactgtttca atacttcacg tcagaagaaa tgagtaacga   14340
cttttaccac agcaaagatg agtggaccgc cgattatgta tcaggctcgt cactcagcaa   14400
gattcacagt acttgccctg cggcgtggaa gtttgaaatg aactcgacga ctaaggcact   14460
ggtcttcggt acgcagtcgc ataccaattt cgagagtaag gcactgtttg agcgccagta   14520
tcgccgcgca ccgaaagaaa gcgagattga aacgtgatc actagccagg cagcattggc    14580
aacgaaatta aaatcatttg gcctgactgg tacaagcggt aagcaatatc cagaactgat   14640
caagatgatg gttgattgcg gcgaagacct caacgtcatg tggctgattg atatgatcgc   14700
acagtgtcag gcgtgggccg atggcgttga gctggttaag gcggaagact acgacgcttg   14760
cgtaagtatg cgccaggttc ttgaaatgat tcctgagcat aacgcctgta tgaatagcga   14820
gacggcattc cgtgagtatt cgttgttcgg cgtaatttgt ggcgttaaag tcaaggttcg   14880
gcttgaccat gttgacatca ttaatgatcc agaatccatc cggcgcatgg gttacgatcc   14940
tgagattcat cctgaaattg tcgtcatcac tgattacaaa acgacaatga gcgcaaaccc   15000
gactgagttc ccgcgcatgg cgttcaacct tggatattac ctcaagatgg cattgcagcg   15060
tgacctgttc gtcaagtgct ttgaggaaac gcgacctgtg gttgtgcgat gctggcccca   15120
ggagaagaag gagccttact tgccgatggc gtaccggatg agtagcgatc agcttaagat   15180
tggtcgagcg cagtacatga gcgtgattca cacctttttca atgtgcgaag ccaatgacgt   15240
gtggccttca tacaacaacg gcgagccgga agtcgaactg gatacacctg attgggtaat   15300
gaaacagttc aagcacatcc tggaagcgta gcactttttg ctaaacacga acgcggtgat   15360
```

```
ttgctataat caccgtaaat caaacgaagt aaataaaggt atatataatg cgtacatcag   15420
ataagttttc gaatgtttca gccgctctaa ttgcagctaa aaagcagttt gccatagcaa   15480
gaaaatcagg ctttaacggt cacctgaaaa acaattactc aaacctgacg gacgttttgg   15540
aggccgtaga gccagcacta aaagagcatg accttatggt tatccagtca aatctggata   15600
cgtcaaccga aaaggtaatg cacattgaga cgctcatcct tcacagttcc ggcgagtggc   15660
ttgcttttca gtacaatatg ccgatcgaga agattagcgc ccaggcttac ggctcaacaa   15720
cttcatacgg tcgccgttac gcattgtgcg cagcgcttgg aatcactcag agcgatgacg   15780
atgcagaaat tgcaaagcgc acggcagcgg actacaaaaa actgatcacc aactgcgaaa   15840
aacttgaaga cctccaggtg atctataaga gcgcgaaagg ttcactcggc gcggcggaat   15900
ggaagattgc agaagaccac ttgcagaagc gcaaggctga attgagcatc ggtagcgctc   15960
gcggtttcca gccagcgaaa aaggcagata cgcaaaaggt tgatgataag attgccaatg   16020
caccttccga gcctgtacaa tctgaatcca tcgaacaatt ctaattaacg gggcttcggc   16080
cccatcaaac aaggaaaata aaatgccaca cgtaatcact ggtcagatcc gtaaagaacc   16140
attcacaaaa gaaggtagca acaataacgg gcgatggaaa atgtatgccg tagaactttc   16200
tgaacgaatg aagattcgaa atcataatgg cgaggatgag acggtttaca gcaactacag   16260
agctacattc ttcgcaaaag aaaatgttat gcagtggtat gatgaagcgt tccaggaggg   16320
caaggttgtt tcaatttctg ctgacactct tcacttatcg tctagacagg gtaatgacgg   16380
gactgtttac gtcaccgctg aaatgatccg acctcaactg caattcagcc agcgagaacc   16440
agcgcagcag cagaatcaag gtcaacaacg gcagcagcaa catcagcctc agcaacagca   16500
tcaacaacgc cagcagcagc aaccaaatca gtcaatgcaa ttcgacgacg acattccatt   16560
ctaaagataa agccccttc gggcttta ttttttacat caacgccaag tgctttgatt   16620
tattatataa gttgatattt cagaccaata aatcgctgta attaagcaag ttttttgtagt   16680 ggatgtgtta gccccagtaa catcaagggc aattccatta aatgacagac tttgaatgtt   16740 tgccccctt aaaattaaat taatacactc accatccctt ggtgttgttg tcgtaacatc   16800
aagccctgaa gtaacgttaa ttctgtaaga tgaataacct tctcttgtat ttattggcaa   16860
tgatgatgat gagtattgtt ttaaagagtt atttccaaga tcaaggatta atcctccaac   16920
aacgccaatt ttattaagga acccaccccca gatcttagag ccatctgccc tacagtttac   16980
tccagaagcg aagttgtaca agccaataga tctatctgct ggattgaaag ctcctatagt   17040
tgcgtggttt gcgccagaac ctttgaaaca tgactcacca acattaagac tgtgatgtgt   17100
ggcgttgctt gtaaaataat aacttccact tgacaaagca acatctgaca ctccattcct   17160
ttcaaggtaa gtaccattaa ccaaagtgct aacaccagaa tctagtatgc cgtactttga   17220
tgtattttga gagtaaccac cgttgattac tgtagcagcg gtaggccaaa gatcggagtc   17280
ttcagggaaa ttaaatgaac catcacttcc gttaaatatt acaattccat aatctgggag   17340
cgcacctgaa tgatcaccac tataacctat gtgattgttt ataagaacag agtttgggcc   17400
attccttaaa agcaccctaa tggagcctac cccgccattt aaaatctcag agtcattaaa   17460
cctaaaacca tagctaaact tttcaattat aaccccatta ttagaggaac caagacccag   17520
atcaagccac aaaccatcaa ccccagagtt attccttgcg ttaaaagcgt gaagtccaat   17580
gcaattgtta aaaccaacgg tagaaagtct aggattgtaa accttgcagt tcctaatgaa   17640
tgcagatgat acatcttccg atgacattct aagtaaagta acgttatttg atgaagcaga   17700
```

```
gagaagtgca ccagcagacc aatacaatct agtgttttga gcgagcgccc atgtctgagt    17760
tgctgatgca acataatact gaccactatt aacaaaaata tccccaccag ataaaaggat    17820
agcccttatc tcctgattag tcatagttgg atatatgttt ttaaagttta atgtttcaat    17880
cttagagtat acattaaggt tcaaccttgc tagtggctta tcagttagat cagacaaagc    17940
catgtctttt cttaaaagtc ttgatgtatc gagagatgcc gcgtaatcct ctgcctcctg    18000
agccgaagtg gctgctgaat tcttgctgct ttcggctgct agtgcgctgg ccgaagccgc    18060
atccttatca gctgatactt tggaggcgtc agtagatact tgtaatccaa ttgatacaat    18120
atctccgtgt tgcgtgttaa cctgcgcaac cttcgcgcta aagtcattag catcaaagtt    18180
attaaatgca tcaactgcat ctgcaacctc agtttcacgt gactgatagt aacgaagcgt    18240
ctcagcaaca tcctgagcta agccctgaac ggtaatccca tcgtgagcaa gaatcgcgta    18300
accagttccg gcaggaacag tttcagaatt agggttataa acattaatct gcgtatcgct    18360
gataatttct gagatagtgt aaatctgtac tggttcagtt ttgaaaacaa tggtagcacc    18420
aacgcgaatc agtgtaagcg gtgctttcca tgtcgtcccg acgccagtaa cctgccatt    18480 tgcggctagc gatgctgttc ctaagtcata aattgccata ataatcaact cctatattgt    18540
tgtttagcac gaattgctaa agtgcagtat agcattgctt taggcataaa aaaacctcca    18600
gaaggaggtt atttagcaa gtcgtttgct ttgtaaactt tctttctaat gcctgtttta    18660
aatgacttgc catcatttgg gatgactaca ccaacagacc tgtcatcagc aatagagagt    18720
atatcaaaat catgatcacg acaagcaatc ctgaagctgc gggacttgtc tcggtgaata    18780
accatttcca tgttataaca ggagaaagca acaaacacct cacgcccccc agtagcaata    18840
tgaacacgta cgccatcaat aaaattatca acaacataag tgtaaccatc aacctgccaa    18900
gaaccaatga cagcaacaga atcacgagtg taatcaccag caaggaattt aacatttgaa    18960
tctccatcaa taaacattaa gttgcagaac tcattaccaa tcccatcctc gtaaaccatc    19020
gagcaaggta cggcatgaat cattgatcca tccttagcta taccaacatc gaatccatca    19080
tcaagataaa taccctcata tgttgtgagt tggcttgatt caactcttac agtccgctcc    19140
atgacttcaa gaacttttc atgatctact tgagcgccca ttttgtaatg ctgagtcctt    19200
gatgcttgct tatttgcctt attaaccact tctacaggga taaggtttaa ccactcaccg    19260
agaacatcga tacattcact aaatgactca cctcgcagct tctggaccca aataatacca    19320
tctcctgaac cgcattggtt gcagataatt ccaccatcac catcttcgct aactttgttg    19380
gtccatctcg cgcgatcgct tcctccgcaa taaatgcatg gctggtgttt ttggtctgg    19440 aaaaacttag gatctgcgcc acatatattg ataagcgcct tatcccatag gccgcgcatt    19500
cttggtaaaa cctctctctt atcgtagtgc atataaataa tctcttaaca aataaaaaag    19560
gttgcaccga ttatggcaca accttaattt tactctttag cttttcgtgc tgcttcgtta    19620
gcggccttaa tcttgcgcca cgatcgacat tctggcttcg tagctaattc agcctcagta    19680
acaacgcgca gcatgtgacg ttttttgcac cggagtgtca gcggctttcc gttgccatcg    19740
aattgcagat ccggtcggca aaaagtcgcg cgaaaccct ctccagttcg cttgtatcgg    19800
ttgtgcgcca gttgagcgcc tcgggccgac atcatgcccc tcttgaacca ttcctcaacc    19860
gcctggcgac taaccttcag ttgctttgcg atattggcct tcgttccgta gaagtcgaga    19920
accatctcca gtcgcgcccg aagcccggcc tttacttcat cttttaaaac gtagtaacct    19980
gaaggtcgtt ttcgttgctt tttgtcttca gttcggactg ttccgttgtt gccgttaatg    20040
gttcgcttgt cgactgcatt catctcatca cctcaatagc acttttttgtt aaacattggt    20100
```

```
ttcgatggct gttattataa cgtcaatcga acgaacatga aaggcattta atactatggc   20160
tatgcgcatt aaatccatta aaaaacagat agaagacctc gggccgcaga ggattaaaga   20220
gattcaggat aaattcacat ttggcgacat ggttccttat gagtatcagt gcgtaatgta   20280
tgacgagatc ggcaagcgca ttgctcgcta taagcatcca ttcatcgtta aggcgtcagt   20340
gtcggcaggt aagacgatcg gctttgccat gatcgcatcg cgcgtaaaag aaatgggctt   20400
gtcgatgatg atactggcgc gtcagggcga tattgtcgct caggatagtg aggagatctc   20460
aaactttggc gttcctaact cagtttactg tgctggcttg aacacaaaat cagcttactt   20520
cccaatcgtt gtcggttcgg aaggaacggt tgcaaacggt ctgtttaagg cgcttggtga   20580
ttttacacct atggtgctgg gtattgatga atgtcaccag gtggattggg aagaccttgc   20640
cgccgccatc gacaacgaag agacgattga atgatgctc actgaaaaag gtgagcgtgt   20700
attcgttgac tacccgaaaa acagcgaagg ttatgtcaat ggataccttg acggcgtaga   20760
agttggcgtt caggtgatgg ataagcaatt gctaatcaga cggaagactg gcaagcctgt   20820
tctcggcacc aagcgaagcc agtacacgat cattatcact gaattgatgc gccgctgcaa   20880
agagaagaac gggaaagaat tacgcatctt cggcatgact ggttctgagt tcagaggcac   20940
aactccgatt gttgtcgata accctaagtt acctgggttc tggcgtgagc aggttactaa   21000
catcgacact aattaccttt ttgagttcgg ttcagttgtt ccaacaatat cggaagtgt   21060 tggtgacgct ggctatgatc ttggtgagtt caaggcatca agccaggacg gaactgcgga   21120
ttttagccag aaagaaatga aggcgatgga aaataaaatc catgacaacg ccagcatgac   21180
aaagcgaatc atggggatgg tcgtagagga agcgaaaaag cgaaatggcg tactgattac   21240
gtgcgcaggt cagcgacact gcaaggaggc agcgagctat cttccacatg gctccaccta   21300
tgagatcatt acggaaaaga ctaacaccaa aaagcgacaa gcaatacttg aggcggctaa   21360
ccgtggcgag ataaaataca tatttcaggt tatggcgcta accactggag ttaacgttcc   21420
gttttgggat ttttcggtaa tccttcgcaa aatcggttca cttactctgc tgatccagtt   21480
gcttggtcga ggtatgagat tgcttaagcc gtggcaaaaa gagatgggaa tggtgaagga   21540
agatcacctg gtatgggatt ttgcgggttg catggacgag ctgggtcagc tttactttga   21600
tccgattctt gaagaggctc agtaccagcg ccgctttgat ggtaagaaag agccgaaaaa   21660
atgtgaactg tgcggaactg agaacagttt ttacgctcgc cgctgcattc acagagatga   21720
aaacggaaat cgttgcgagt atttctggaa gtctcgcata tgtgaagacc agattgatga   21780
tcgcactggc gaggtgattg ttaagggatg tggcgctgaa aatgacgtag tggcgagaat   21840
atgccgttgc tgtgacgtga gcctgaaaga tcccaatgat aacctgactg gtaaggctta   21900
caccaaaaac gactggtgca cagttaacag tttcgaagtc acgctgacac gtaatcatac   21960
tggcattctt tatcggtacg acctgacaga ctcagttgga gttaacttca tcgcgtatga   22020
gaagttcttc cctcagtcaa cggcacaggt atgccacacg atatgaagc agaaaggggt   22080 attacctcac gttcatgaca gtaagatcgc aaaattaatg gcagcttaca gaagtgcgaa   22140
aatgatttta acaatgctc accacatagc gcatccggtg cgggtaactc accgcaagaa   22200
tgcaaagggt gaggatatta tctcacgtaa ggattttgga ttggacggta acttatgatc   22260
acagacaaag gcgactacct ggaatattac actccagaca aatctgacac atggacggaa   22320
agcaagcacc aggtagactg cgtgacttgg actaaggtta ggcatgttga tttgctgttc   22380
tggcacgccg ttaatgagaa caagaagcac atccacacgg cgctaaagga tgctcagagc   22440
```

```
gggttattga aaggggttag tgattttgta ttccttctag gcccgttcgg taaatatccg   22500
ttcggggcca tagaattgaa gcgcgtcaat aagagcggga aaggcaaggc atcaccagtc   22560
agtaaggagc agaaagattt cctccggcgc gtgcgtgagc gtggcgggtt cgcggcggtg   22620
gcatacggtc aggaggaata caagaaagca gttgctgata tgctgaatag cacgaattgc   22680
taaagacgaa gcggtgaggt ggtgtattat cacctcatcg aaacgaagta accaaccaag   22740
gaaatcaaaa tgaaaagtc aatcatagct ctactggcag ttgtggcaat ggcaggttgt   22800
gcagaagata ccaagtttta cgattgcggt aaggaatcct tcacagtaac caagtcgcag   22860
attgtttcag acaagggcgt tgttattgag cgtgaaggcg atcactacga actgcaaact   22920
ttcttaggga aggcagttta caacgtgact gaaagtcagg tcaaagttag cgtcggcggg   22980
ttcgtcgctg ttaataactg caaagttacc gaggttaaat aagatgatcg actcaaacga   23040
caaggatact catgacgcat tcgttagctt tgagcagatc gagcgtgaaa acttcgtggc   23100
aaatgccctc gttcctggta acgggcacta ccaagcagtt aagcctgaca cattttatca   23160
tgtaactgga aaacgatacg ccggaagtaa gacacctgac gcagtaagag atctttgggc   23220
caccgacatg gagctgatct catggatgga gtcgcgttat ggaaagtatg acatcgacgc   23280
cgccgccagc gctaacaatg cggttttgcga aaagttctat agcgagcaat tgaactgcct   23340
taagatctgg tggggcagaa ataagcacat atggcttaac cctccttact cacatccaga   23400
tcctttcgtt aagaaagcga ttgagcagat ggagcacggg aaccagattg acatgctctt   23460
gcctggcgat aactcgacgg cgtggttcgc tgaggcgaga cgcaatgcgg ctgagatcat   23520
ctggattgag gcagagataa cagaaattga ccagcaggaa tactgccgaa caggacgact   23580
agctttcata gctggactga ccggaaagcc tgtggatgga acaataaag gatctgtcat   23640 cttcgtcatg cgaaagctga agaaggtga ggaacagaaa acgacgtatg ttagcgtctc   23700
tgagatttgc cctggcgtaa gccgaaagaa accacgtaag cggagtgttt aagatggaaa   23760
agttgcaatt tgatttaact gagcaggatc agttccttt atttcgcggt cttgtttgca   23820
aggctcttac aatggctggg ttcaagggtg atgcttggga attctcaaat cttgacatgt   23880
catttgaaga ggtccaaggc actccatttg aatcatggtc aagatcaata gcaaaagatc   23940
tcgcagacta taagcgcgat tgccctgagg attttcacga atagcacgaa ttgctaaaca   24000
tacccgccgc tgtgcgggta tacttctttc acgccaacga aacgaggaat caacatgaaa   24060
aagcaacctt ttgttactca caaacacgca gcataccgta acaaggtttt atttccgcac   24120
ctgcttcgcc tggctaacga tagcgcaaag gacgcgatcg cacttggtaa ggacggcggt   24180
ctggacgagg ttattgcggt gacttatctc aagggcgctt atggtcactt gccagttgct   24240
gactatcagg ctatgtcggg gagctttgac atttatggta actgttgagg ttggacgaca   24300
ggcagtgtgg actcactgca aagaggcagg gataagtgaa gatattgcgc ttatatccaa   24360
gtattttgac atcaaagata tatgcgtcat tttcaacgga aagatgacgt atatacacga   24420
aatgccacgt aagctgatca gggttccggc aaatccggtg aaaattgact acaaggcctg   24480
cattcaagca acgaaagacg cagcgagaag atataaatga acttacctgg acttgatttt   24540
gacgctgaca aatatccgac ttgcagcaac aacgatgaga cgttcgcgat catccctttc   24600
gctgactggt tgccttctga cttcgaagat gtgccatgtt cgcgcggtgg cggatatcgc   24660
ctgatgtatt ttagcccttc aactggtatg atggttccca gcgaatcaga gagtgcaggt   24720
gaagcgattc agccagatac tttaacaaca tggttgaaaa agatttgatg cgctgcttaa   24780
ttcctgtatt attaccgccg ctaattggtt ttattatcat ctacttacta acacgataag   24840
```

```
ggtttacaaa aatggctatt caaaaaatca ctgacgaaca attcattgct gaacgcgaag   24900
ctggtaaaac gctgcgccaa atcgcccagg aatacgggat gaacattaga actgttgagc   24960
agcgctcaag ccgcctggca aagcgcggtg agttccacgg aaataaacac gtaagagtac   25020
acgtaccaga gggttttcag gttaaaggta catcaactat gattcgcgct gacggttctg   25080
aggttgtgcg ctgggttaag accgatcagg acaaggaaaa gttagccgcc atgatggatg   25140
ctgcaattga agcattctgt gatgaactac cacgcgcggc ggctcagcct atccttggcg   25200
aacctcacta cgatgaaaat ctcctggcgc tctatccggt attcgatctt catattggcg   25260
cgatggccca caagcatgaa tgcggtgaga actacagcac cgacatctca gagaaagtgc   25320
tgaaaaactt ctttgattat tctgtcggcg tatcaccgaa ggctaagaaa gcagtcctgt   25380
taatcggcgg tgacttcctt cactctgatg gcctggacgc agtaacgcct gcaagcggtc   25440
acgtactgga tcaggatagt cgatacgcca agatagttca cgttgcaatc cgttccgtac   25500
gccgcgcggt ggcgctaatg ctggataagc acgaagaggc cgaaatccag atcattgaag   25560
ggaaccatga tcaggcgggt atgatttggc tccgcgctgc aatggcggca tactttgaag   25620
atgaggcgcg cgtaacggtt gatacgtctc ctatgattct tcaccgtaca aagtggggca   25680
aaacattgct tggatacact catggtcaca ccatgaagaa agctgatact cgactggcgg   25740
caatggcgac tgacttccgc gaagagttcg gtacgagcaa atatatctac actcactcag   25800
gacactggca tcaccagacg atcacagaag gcacgctggg tattgatgag attcacggtc   25860
agcttggcgc gaaagatgcc tatgcagcgc gcggcggttg gcgctcatat cgccaggcgg   25920
cggtaattgt ctactccaag gagttcggcg aagtcggtcg ctttgtttac cgtcctgaaa   25980
tgagcgacat ctgatagcac gaattgccta acactatagc tccggaaggc gctatattca   26040
tgtctcactc acagaggatt caatcatggt taaattattt tgcgttaaga acacatctaa   26100
aaccctgcct ttcactgtta acaatccgta cagcgccgag tatcaaggtg acggtaacta   26160
caagatttac ggcgacgata tgacgtggat ttttgcgccg attgatggtg cgctggttga   26220
atttattatt gctgactagc gcattaaaaa cataacgtta cgaacgggga gcctttaggc   26280 tcccctttttt tgtgattctt ttctgtaccg tgataatgta ttatgttttt tactaactga   26340
gatattgaca attacataaa tggtggatca catgaaagag gtattaaaca ctgtaacggc   26400
tggtactggc ggggcatctt tcgctggcgc tgcaacgggc cagctggcga tcgcagggc   26460 gacgttcatc ctgttcgttt gttttggcat ttggggtgct tactggaaat atcaggatag   26520
caaagccatt cgtcaggcgc ttgactcagg agacttgccg acggctctta aactaagggg   26580
taaataatga tgagcgtaaa caggacgctt gctagtattt cttttggtgt agctttatcg   26640 ctaacgccctt cacttgttga gaagattgaa ggcgttgagt acaagccata taggatatt   26700 gccggagttt ggacagtgtg cgctggcatc actggacctg acgttattct cggcaagacc   26760
tacaccaaaa gagaatgcga cgcattgcta tataagcata tcgacatcgc caagcgtgag   26820
gttgataagc ggattaaggt tgacgttccg gataacttcc gtgcggcaat gtacagcttc   26880
actttcaacg ttggcactgg tgcttaccgt aattccacta tgctgagact tactaaccag   26940
ggtaaactac ttgaggcttg caatcagcta tgggcctgga cttactttaa gaatccgaag   27000
actggaaaga aagaacggtc aaaggggctt aagaatcgac gggcgttcga gtatcaatat   27060
tgtgttaagg agctacagaa atgagttgtc taaatttaca gcgtgctttg gttatcggct   27120
tcgtagtgtg ggccttgttc gtgttatcag gttgttcggc aacatctgcg ctgactggtt   27180
```

```
taattggcag caagccagaa atcagtgcgc aggctggggc tgagaacgtg aagcaaacgg    27240
taggcgttac cggaaaggtg gataagtcaa acgacaacga cactactatc aaagattcaa    27300
aggtaggaaa ggttgatacg tcaaacggga agtctgtcag cacctcaagc atcaaggctg    27360
acaccatcat cgctgataag attgagatca ggaacgatga ctcgaaaggt aatctgattg    27420
ccggactggt attcctgttc attggcatcc tgatgattgc tctttcaatt tggctggaac    27480
gacgcaaaaa ataaaaggag ccgaaaggct cccttttttt atccaaatct ttgcaccagt    27540
agcaacaatt caccttcatt attgcacaac gtatgctcat cacgtcgtcc ggcgcgcatg    27600
gatgagttaa gcattgagat aagggcttgg ttaatcccgt cctcactaat gccattctca    27660
gaactgcatc tgattatcgc gtcgattacg acctggcttt ccgataaact cttcatcgct    27720
catcttctct atgttcatca tctcccatgt atagcgatcg ttctcgccgc aatagcacct    27780
gaaatgaaat tcaaatggcc ttttttgcgc cccttttggac cagtaccagt tgttcacgcc    27840
gtcaaggtat ccttcgccca tgcatcttgc gatgaactcc tttgatgctg atgatgcgaa    27900
gtagcgaggc gtaactccgg cagccttcgc cagtcgctcg cactcccctat gcttgtatat    27960 gaataccgcc atgtgctgac ggttgaattt ttcatagcct tcgcaaaaac ggtacagatc    28020
cagaagaaac ataattttacc ccagcagtcg cggattaatg taaattttat caccaatcag    28080
gcacgtatag ttttctcat caagcatagg gatcagatgg tctttgattc gagtcattac     28140
gccagcctgg ccctcgaatg gcttaacctt acgagccgct tcatataggg atctgacacc    28200
tacaacgcct ttcccgttct taccttgctt gatcagaata tcgatcagct tattcatctc    28260
agcatggtcg ccagcatgac cagcagcgtt tgcagatgac agataagtct tactcagctc    28320
ctggaacata attaccgctt cctgcattgt gtcaagctca atctctctgg acttcttcgg    28380
actcccgcca ttgggattaa accagttacg cacagtgtga agaacagccg cgatcctgat    28440
agcctgctta tcgaacttac ccagcgcgcc gcgaagcatt gtgtgtgaat acttcccgcc    28500
gtccgcaagg tgaggttcca tatcctgacg cgcacggttg agatatttca tcgccgacgt    28560
gctcactgtc aggttgactt cgtgttcgct catgatctca tggaccagac ggaagtagtc    28620
cgccttgagt ccgccatcaa tcggctcgta tgttgattcg ccttttttcgt caacgaatac    28680 acgctcgcca aggaatgact tctcacgcac aagcaagaat cgctcggata caccgatacc    28740
acgcgcgcca gcattcatga tcgcgttgat tgtttcatcc tgcgcaatta cagatatgca    28800
gcccatcgca ataaagctca tgttgttgtc tgcgttcgca cgggcgatag atacgttacc    28860
agcatcccat gccttaagca caagttcgct gttcgttttc tttgagccat caccataggt    28920
catgcctaac agtgagttta cgctcgtcgc ttcatccgag atcacagaga agttaccctg    28980
gcggttgttg attcgcgcca gaccttccgg cgtggtgtcg gatacgggga atacgatgtc    29040
acaaaggcgt tccagttttt cttccagttc ttcttttttcc tcaaacagtg ccgccatgtc    29100
ggacggtgat ttttcctgct tcatctcctt ggatagagca gatagtttag ccataatctt    29160
cttgcggtcg cgctttcgga tctcgttgag tcgctcagtc tctgcgatca tcggggccag    29220
cgaaagtgag ttgatggctg atttacctgt cgatggtggc tgactggtta cgacgtaaag    29280
agcggtcggc tgttgtgttc cgtgatactc aaccgtaaat cggcccagca tggcggctga    29340
tatgcatccg aggaaatgca tgtaagcgga cgactcgggg aattgaactg aacgagcggc    29400
attgcttgac agcttaccaa cgacatcata atcgttacca agtgagataa ccggatattt    29460
gtcaccgcct gagtcaattt ctgttggggc tttccagaat gattggctct gcctgtatcc    29520
gttcgcattg atggcaacgc gcaaaggtgg caggttatcg gcagcggcta cagccatgac    29580
```

```
ctgatcgatt gacaatttat cttcgttgaa atcaaacatt aaaaaactcc ttagtggtgc    29640
gctaatgtta acgcacctat ggtaaatccg cttgccagaa aatgctactt atttgtacgc    29700
cgcctgccac ttgtacgtac cgcagaggct catgaagcca acctcttcgt ttcggtaaag    29760
ctgccaagca ttaccatcct catcgtaaat gtaaccggca gattggccaa ggccagcatg    29820
aatatttacc tgatagcgct taccttcttt gaagtctttt ttaactgctg acctgtgatt    29880
aaccttcgtg cagtaaagag ttttttgtctt gatgtactta ccgcgttctt ccaggttaac    29940
ccatttacca tctttcttga tttgctctac accgtcttta acacgagctt tgtataatac    30000
gttttcgttg ctaatgaagt ttttagttgt tgctgtcatt ttgatttcct ttgcgtgttt    30060
cgtttcgatg agatgaatat acaggaaaag ccccgaaggg ctttagcaat tagtgctatt    30120
tgttgctttc atatagtgcg cgagcaaagc cttccggtgt taatgagcgg agtacctttg    30180
tctttgcaga ctttccgccg cagtatttcc aggcccagaa gaatccaatg ctctcaactg    30240 gcttttaat aggttcaaca aatccattgc cacaccaaat gcaagtcttt ttattgtaag    30300
cattacgagg gggcattctt gggtgataaa catcatcgtg atcaacgtaa ccgccataat    30360
cgcaaggatt gaaatagaag tcaggcttac gccacaggct tgacagcttg cctaccggat    30420
tctcaaccat ccatggtgcc tggaagtgat tgccgacttc ttcgacgagc ttcgcgttag    30480
ccagggcgta tgccagctca tcttccccgc gctcatgctg tgatccagac tgagagaaca    30540
gcgtgcaatc aggaaagccg ataaccattt gcgccggagg caggccgagc aattcacact    30600
tagtgatgaa atccttgtca atccacatgt tgacgtagtg gatgttctca tgcttcatct    30660
tgatatggta ttcgccatga ttgccggagt ccgcattgaa gcagtagacg gtgtgaccat    30720
cttccgccca tgggaggcca gcgataccag aaccgtcgaa caagcagtaa attacctttt    30780
tcatttcttc ttagccttct caattgcttt ctgtgtgatt tcgtaactgc tttgcaagtc    30840
ttcaacctga gcgatggtgc tccatggata ccatccttga cctgagagct tcgcgatcgt    30900
gtcgttgtcg tagtagttca aatcggatgg cttgagcatt atttcacctc atcaaacgtt    30960
gcgataccaa ggataaacat tccgaccttc cagcctgcga tagcaatcca gccagaatcg    31020
tgcttgtgcg gtcgctcagc gccattaata acccattcgt tcgggattgt cttaccgtta    31080
atgattagcg gctcagcgtc gtatacagag cctttacga atggtgtcaa aaccttcttg    31140
tctgtgctgg cgattacgtt agtgcacttt accttcatga tctcaccta gaacgggatt    31200 ccgtcatcaa attttaagcg gtagtcgaag tcatccccga ttccgtctac tgactggttg    31260
ctttcgcttt ccagatccat atccataacg cccaatacgt catcgagttc gatgcatccg    31320
taagcaacct tgagcgccca ctcttcattg agtccggctt caagtgccgc gcggtggcgg    31380
ctccagaaat tatcttgatg cactgttagc tccaggaatt gatgtaaagt gagttatcat    31440
ttaacaggtt gatcatctca gtacgggtaa ggctacggat gattgagcct ggatgtgtgc    31500
caacaacgta gcggtcgaac tcacggcgcg tgatggtgat ttggcttacg cctgcggcgc    31560
ggtccagctt gacgatcgca cggcctttg cttcgatgtg tgctactacg ttctgagctt    31620
taactgacat ttttacttcc tctttgtgta cttcgtttcg atgaaatgat tatgcctcaa    31680
tccgtgaggc ttagtttagc aattcgtgct atttaacgat ttttggtgg tcgtttacag    31740 tgagcataaa acggcgttgg cggaaagcat ggatgataac cagtcaggcg ttgacgtgcc    31800
gctttgccga aagcagcagc cgcatttgt tgttccattg caatctcacc tttgcggaac    31860
aatcgtcttt tactaaaccg atgccccatg aactcaacgg caaagtagtc aatcggatcg    31920
```

| | |
|---|---|
| agcgctacac gcttttccat gaacaccttg cgacttgatg ccaggtatat attgctaacg | 31980 |
| ccattcccga tacaggatcg caagctattg tagatcgact cattgaattg gtgctggaag | 32040 |
| cgccaggctc cgtaggccca catataaacc ctgccggatg gcgtaacaaa ccttacctttt | 32100 |
| ccgtcagttt ttcccttata gataacaccg tgaacaatgc tcatttgtca attccttaaa | 32160 |
| ttagtgaaat atcaacagtg attttggcct ggccgattac ccgtgccaca ccaccgtaaa | 32220 |
| gtagcgccca ctcaatagtc ttagcattca tagcggttgc ctgtactggc atctcaccca | 32280 |
| ccaggcggaa cacttcagga ctttagttgt cgcaacggat tagatactcg ttaccgctgc | 32340 |
| caatcagtgc acattcttgg cgtaactcca tttctgcaac tccgcttcgt agtattcata | 32400 |
| gttgttgaaa ccatcgcgca tgttcatctt ctcgcaaacc tgcttagcca tctgttcact | 32460 |
| gaggcatacg cagtgaactg tcgtatcgta attcggatca cacggctcag acatcacgat | 32520 |
| gtagcaatac attttttacag tgctcattta ttttctccag ttctcttcac tcgtttcgat | 32580 |
| ggagtaataa tagcgaatca cacctgatcg gtcattagca aaaagtgcta ttcgttggat | 32640 |
| ttatggattg ttgcagatat tgcaatgatt atcatgacta ttgcacatac agcaatattg | 32700 |
| cttccgatgc aatgatgttt ttgattgttg cgaattgagc gatgattcat tggtgggggg | 32760 |
| aatgatgggg tgagatctga tcccatgatc gcctggtagg attttttccgc cacacgtttc | 32820 |
| caccgcatac gcgttatgca tgttatactc tgtagacaaa tccatccggc gtggaatcag | 32880 |
| gtacgcctat aacgcctagt tacgctatgg ttacaataaa atatccttat ataacaacct | 32940 |
| tttatctata ttattattat tattatatat atatgtagat aatgtagata agaggtattg | 33000 |
| gatattgcga tagctttcta tgatatattc tgacacttgt aagaatggga tgacattgta | 33060 |
| ggaataaaaa ggcatatatg gggcaatcct ccgcgaaatt tgatgtacaa gctgtacata | 33120 |
| gtggttacat tgagctatat ctggctcaag aggtcgtaaa acgtaactaa gtcgaatatt | 33180 |
| tgcatcaata acacttgata acatgtaacc atgctggtaa tattgcaccc atcttaacga | 33240 |
| agaccaccaa tcaggagtaa tatctatgtc aaatcataat caatccgtaa gcctgggaga | 33300 |
| tgtcgtccgc tacatggcgg agcaagcgct caagtccgag aaccgaagtt accacgttcc | 33360 |
| aatccacctg atagctcgcc agatgtacgg actcacggct gatgatatgg gcagaatcaa | 33420 |
| tgccgacgac cttgaggctg gcggtaagta cagcgttgca aagctgaaag cctcgtacgt | 33480 |
| ctctaacacg gttgccagga tgccagagat tcaggcggcg aacgttcggg ccaagctgtc | 33540 |
| aatcaaggat ggcgacttcg gggatgatgt cgatgttcga tgtgcttaca tcaccctggt | 33600 |
| tgatggtgct atccaggccg gaacacgacg caagggtgac gaggaaaagg aggcggtaat | 33660 |
| cgttgaaagg ttcaagtctc ggctgctcaa gatcacaccg aacgttatcg acctgcaagg | 33720 |
| tgagcagaaa gaaggtgcgc tcattgccct ggctcgctac catgaaatga ttaaggaaac | 33780 |
| caaataatga gttacttcgg gagcgaaaga atgacaggcg agcagatatt caatgaagcc | 33840 |
| agtgaaagcg gcatgtcacc gcttaaggtt gcgatcagtg caaatggcta tcgcgacacc | 33900 |
| ttcaaatatt ggtcaagctc cgaagagatg tcgtgcgtca agctgagtta caaatacggc | 33960 |
| gtcgtggtgc ataagattaa gcgcttatgc ggcaataccg gaatggtttg tgtgagccag | 34020 |
| ctatacagac aaatcagaga ggtcatacca ttcgtcggac gtgatggcat atacaatgac | 34080 |
| ctgagcaata acatcctgcc gtcactccag gacgccggaa tcatctgccg gattggcgac | 34140 |
| aagatatttg tgcatccagc cctggcggga atgcatgagc gagacgtgta cagctggtgc | 34200 |
| agtcagtacc gatctgatgc gccacgctct cactacgttg agccgattaa gccgccaacc | 34260 |
| atccatggct atgatgccga tgaggtggag aaggccatcc agttctaccg gaaagcgaaa | 34320 |

```
actctcctga acggtgaata gcacgaattg ctaaacaaca aatcgggtag tcagctatga   34380
ttaccctatc aacaacgaag aggaaatgat tatgtaaact gtacgcattg acgatgttca   34440
ctttgaacaa gcagaggggt cagcgtcacg atgggaaccg ttcgcgggca tgttgtcaac   34500
cttgaattcg atcctgacgg ttactccgac tgtcaaacgc tgatgcaata ctcacctgac   34560
gcggcccgca agttagcggc ggcattaatc cttgcagcag acgaagcgga ggggaaataa   34620
ttatggaaat tttacgcatt gaggatgtgg ttggtgatga tgccgaggtt agcgttctgc   34680
tcaatcggac tggagtagtc aaggccgtag tctccattga cttcgatact gacgatcagg   34740
gcgttaccat gatgcactac acaccagagc aagcacgcaa gctggcggcg gcgcttatcc   34800
tggcagcaga agaggctgaa aagcaatgag agatattcga gtcaattcat catggaatca   34860
ggaaacggaa atctcagtaa tcaaggttcc atttggcaag atgcgcaagc gcgtgcacct   34920
ggacctcgcg ccagattcgc aggcagacgg cgctggcatg acctacacag cagagcaggc   34980
tcgtgaactg gcggcggcac tcatcaaagc ggctgaggaa gtggaggaag aagaaggtga   35040
tgagtaaatt caggatcgca ttgattgaca cgactacggc cttctgtcat ccggtcaagt   35100
ggtatgcaat ccagaaaagg gtagccctgt tctggttggt tacggttggg cacaccagcc   35160
agttatccca ggctcgctac tggctgcata agtccggcgc accgcatcgc aaagagaaag   35220
tattgaaggt ggtagaatga aaaagttaat cttaattgca gccctagcac tggctggatg   35280
tgatttcgga agcacccgtg tagattcaga ggctcggcag aagatgcaag tgaatgtcaa   35340
cgatcgcgtc caggttgtga agattcagga gttcagggat gaactggcat atgagaacgt   35400
cagagcgata tacgtcatca ccgataagga cactggtcag gaatacatcg gcttaagcgg   35460
tgtcgggatc gtggaagttg gtcgccatgg ttgcggcaag ggatgctcca gagaagatga   35520
acgatagcac ttttttgttaa aactgccgtg agtgcatttg ctatagtgca ctcattgaag   35580
tgaaacaatc aactaagggg taatttatga gcacaaccgc cgtacgcatc gcagacgact   35640
acaacgagca ggccgaaatt gaggctgtga agattcatag caatgacaag gtgactttca   35700
aggtgcgcct tgacttcaac cctcacgaag aatcataccc aagtagttac atgctgtaca   35760
cgccagacca ggctcgccag ttagctgcgt atctgattga agctgcacac agagctgata   35820
agggtattgt atgattaacg attatgaaat taagaaagaa agcaagatat ttaacgattc   35880
agatggtgat tcttgctgca tttacacgag aaagacgctg ggagttgtaa ccgtcgagat   35940
ggtgattgaa cacgaatcag gagcgttccc catgagggag tcgacaacag tccgcgcaat   36000
gggtgaacac cttatcaaaa tggctgacta catggagcgc cacaatgaac aatgaagaaa   36060
tggttaagat ccgcattatc aagtcaccat atagcggagt ggataaaagc aagctgccag   36120
tggtagcgat ggcctggaaa taccaggaag aagggcttga accattttac atggttgacg   36180
ctgacttcct tccggcgctc agcaaaaaag gaatggcacc gggcgactgg ccatttgcag   36240
aggatgaggt tgaagtgcta tgaagttcaa attagttgac gtgctgcaat tgcttctttt   36300
cgggttatcc tgggtgcttc tgttcctggt gatgattatc ctggtggtgg ttaaatagca   36360
ctaatcgtta aaccttccgc aaggccattt gatatagtgg ccttattgaa gcagatacaa   36420
ccaataacag aggattcaca aatgaaagta cgtttactta acccatcaat ttacgcagac   36480
cttgattata ccaagctcca cgagaaagag acaaacccac gagatcccgg atcatatccg   36540
atcgttgtgg gggggttct ttgatggcac tgaatttaat aatagttcaa tcaaggttgg   36600
tggtgacgag cttgatcgag tattcaaaag ctatttcagt agcggaaagc caatgaactc   36660
```

```
atgttacggt agcgaagcag ttcttggttg gtggaacgat ccaggcaagc ctaactcatg    36720
ggagccagtc ggcccgttcg actactggaa caaattaaag gcatcacgag aagttggcga    36780
aactgtaggg aagagttact tatgattatt ttatgcatcg tgctttacat cctgggcgca    36840
cttcctgttt acgcaattgc aaaagacgtt agcaatagtg ataacaactg gtacgacatg    36900
gtgatcgttg ccgctatctg gcccattgcc attgcgttag gagtggttaa aggcgcctac    36960
aaaaagttga aggagcaata atcatgcaag tctacactaa cagtaaaggc attgaatttt    37020
gcgcggtcgg aggtgtcgtc ctgcgtactg gtggcggata cgggattatt aacatctcag    37080
gcatcacgca ggatcagttg gtaaagggca tccaggctgg catctttacc tataactcat    37140
cgctgacggc taagcagtac gtcacacttg agacggcaat tagcgccgga gtcattgaat    37200 agcactttt gttaaaactt gctcggagac attagatata gtgtctcctg tcaagtgaac    37260
acaaatcaac tgaggaatca cacatgaaca gcatcaaccg ttttaatcct gtagcagtag    37320
caaccagcgt taacattcac ggcgtcagaa tgcaagcctg cgacgatggt cggtgggtat    37380
cctacgatat gcataagcaa gaaattgagt cgttacaggc gcgtttaaag gcgttagaat    37440
cgactcaaaa acatcaaatt tctgcatatt cgattatcgc tgaccatgtt gagcaggcaa    37500
tcaaagaagc tgtaggtaag ctggtgcacg aagcctgtga acaattactc aaggatttgc    37560
ctaagtacaa tggcgatccg tgtcacagca ctgtcgatgc gttcgtgaat gagcttgcga    37620
ctggcccagg taagaccgtc aagaatgaca cctacagcgt cgcagatgaa ttgacgaaga    37680
acggcaagtt cactttcggt agcaatttcg gtgaaggcaa ggcgcttacc atgtcaaccg    37740
cgaaaatgga accacgcagc ggcggttacg gttatgtcaa tcgtaacgta tgggcggtgg    37800
gtgaatgcga atctgcacgc gatcgcaagg tggcagtttg ctaccatgtt aacggcaatg    37860
cgtttatcaa tggttgccag tacgattatg aagttgatga gtgcgagcca ggttgcgagc    37920
ctcgccttat ccatatcgca caagatgcat tcatctctga tttaaaaggc gattaccgat    37980
ggaaagcaaa gagaattggt aaggttatga atgccaatgc aacgctcggt gacgcatacg    38040
caatagtaaa tcctgatggt ggcgtagtgg ctcagttcta tatcaaatag cacgttttgt    38100
taaaggggga ttcatcctga ctggtataat ccccacatca accacacgaa aggaagttaa    38160
aaatgaacca gctttacaca atgattaagc atcaccttca aacggaagca gtaaacaaga    38220
aagtttacat atttgatttc gatggtactc tgtcggacgg ttcgcaccgc cttcacaagc    38280
taccgacaaa tgacttgcac ctcactgagt catggcttga atttaactca ttgagcaagt    38340
tcgatcagcc attccaggaa acgattgacg taatgaatag cctgttcgct tccggtgctt    38400
tcattatcgt tctcactggt cgatctgacg cagtggtcga ggaatcaacg cagtggctgc    38460
atgatgctgg tgctaattac aacgttctgg tcatgcgcca ggctgatgat aaccgcaagg    38520
acacgatcat aaaggaagaa ttttacgct acattggatt gcaccgcatc actgcggcct    38580
ttgatgatag tcctagcgtt atcgcgcact tccgaagcct cggcatcact acctatcagg    38640
tgtgtgacta tggcgacaac gtgcactccg gccttaagtc tcacggcgta gacaagaaag    38700
caaactaacc ataacgggcg cacatcgcgc ccactactca ggaatatcaa aatgtcaaag    38760
attatcattc tcaacggtcc agcttcggtt ggtaaagaca cgatcggcaa cgcgctcgca    38820
gcggattaca actgcatccc taccagcttc aagcgtccga tgtttgagat tgcggcatcc    38880
atccttggtg ccagagcttt ctcaaagttt atcaccgcat acgactaccg cgatcagaaa    38940
gagcagcctc agaaatttct cggtggcaag acctgccgtg agttcatgat ctggattagc    39000
gaaacagtgg tcaagccgct ttttggcaat cagcagttcg gcaaattgat gagcgaacat    39060
```

```
atccagctgt gtgatgaagg cttctgcttt gtttgcactg atggcggctt ccccgacgaa   39120
gtgatccgac tcgttgaaga tggtcacgat gttaccctgg tccgcctgtt catggatggc   39180
aagactttcg ctggcgatag ccgtgattac attcgcatca aggaatcgca ttttcctgat   39240
tacaagaaat ataacgagca tgatgtgcat ctggtcaatg gtgatattga aggcggtgta   39300
atggcagtgg ctgaggcttg cggtattagc tcaccagtta cagaggttga tgtttacgag   39360
tgggaagatg gattaccctg gtaaatagca ctaattgcta aacccgctcc ggcgggtttt   39420
gttatagtta tttcacacca acgagaggg aagcaaaatg attactatca acctgtcaga   39480
taagcaagcc gtaatcctta agcaactact ggcgactcag actatgcagt gctcagccga   39540
tgagttctca gagatggtta aagaggttcg cactcagatc aacaatcaac aatttgacga   39600
aaacgaaggg gaataaccat gaaattacgt tgtgttaaaa tacatccagg gttagcgatg   39660
ctgtttaatg attactttca ggttggtcaa gtatacgagg ccaagcgccg acctaaccgt   39720
cacctgaacg tggctgatgt cattgatggt tataacggtc tttcatggta cgccgtccag   39780
aaaggaagca agtacaacct gaatctcgca agtggcccag ccgtcacttt cgtgcttgta   39840
aaaggtccgc gccgcttagt agtgactgaa aaacgtgtaa ctaacgtgtt aaacgacaag   39900
cgtaaatttc gccgcatgtg ccgccagtac ggtaagcttc gatttactga gcctgggatg   39960
ttctgcttta tcgccttcgc ggcaatgaaa aagaacgcac gaaatcacca gcgatagcac   40020 ttttgttaa aactcataat cggggtagct gtatagttac cccatcgaaa cgaacgagga   40080
agcagaaatg aaaattgaaa ttatcgacgt taactatgtg acagatgacg acgcccttac   40140
cctggaagat tgcggattta agtcggcga cgtaatcgaa gtgtcaggta aatacaagga   40200
cggcgacctt tcaatccaag ctatccgtga acagagttc gtgcatgttg caacgaaat    40260 cagcattagc gaaaatgaat ataaggtgat cgagaaatga tttacattaa cacatacggg   40320
gtcggcaagt tcggtaaaga gattcaccgg accgttcacg aaacgaagga atcagccgaa   40380
gcggcacaga aagttctcgg cggtgagttc aaggcttacc gcgaatcgga ggactcggtt   40440
gaatgctggc aggttgagca catgcgtaac gttctggaaa gtgaggtgtc agaacttatc   40500
gacaacatga catgtcacga ccctggcgga ccatgggaag aaccaggctc accggaatgg   40560
gattgcgcca aggttgacac aatgaacaag atcagcgaaa tcattgatga ggtttacgaa   40620
taatgtttgg attaaccgat ccgcagatga acgcagtaaa ggccaaggcc aagcaattaa   40680
acgcagcgta tgccacccta agcaagaaag atcgcaaaga tgataagctg gttgcctcaa   40740
ttattaccaa gcaccatgag gcagtagcga ccattatatc gcgtgacaaa tttgtgtgga   40800
ttgctggtta tcttaagggt ctggttggca acgtgaaaaa cggagaaagt atctatgagt   40860
aagatcaaga aaggtgacgt gatcaagtgc atcggcgcgc gcggttatga gttctttact   40920
ggctgcgagt acacagtgga aaagttgat tcccagggat tcgtttacgt ctacagtgac   40980
gaggggaaca aggtagcgat cgactaccct gtttgcccga cgtatggaac ttttaaaaaa   41040
gttgattgac agacatctca ctgactggta tctttaatct cgtaaacaga ctaggccacc   41100
aagtggcaac gagcggttcg taagccgcaa attgaaatag cgcatcgcca aaagcaaagt   41160
gtaagtcgca aaaaaatcg gggcattgtg aaagcccgcc ggactccgta accggaccta   41220
acaatgaggt ttgatatgtt tgaggtcaag ctaactattt tgctaatggg gcgcgcatgc   41280
gcatattgta agcaaaactt tgaagcaaag gttgaggcca gtagcgccga agaagccgtt   41340
tcaaaggtga aggaaatgag cggagtcgat acaacgactc ataaattttt agttaattat   41400
```

```
gtaagggta tttcatgctg acgtttattt atggttttat tttcgcttcc gtcctgatca    41460
tttcgttatc ttgcgcctgg gtagctaaga taatcaagcg cggacaattc gcacaagcgc    41520
gatacgatga gaagaaaaag cagtggcgag tatccggtaa gttcatctca gtgtttaacg    41580
agattaacga tattcgatcg gggcggaagc ctggggccat caaatacgtt gactgattca    41640
tttaagcatc cttcggggtg ctttttttat gcctgcaatc tggtataatt cattcctatt    41700
caacaagggg aaacaactat gaaagacgaa aatttcacca gtcacgcgaa cgagaaggtt    41760
agaatcggta acttcaaaga gctatacaat aaaaagtatg gcgacattgc caacctgaac    41820
catcgtcacc caatgacgcc tgagactgta ttcaaccttg cggttaaata tttctcatgg    41880
gccgaggacc aggcaattaa ggcaatcgaa acggcgagct tccatggtgt tgtcactgag    41940
aacctagtgc acaagccgcg agtgttcacg ctcaacggtt ccagcttta ttgcggcgtt    42000 acctccggtg cgatccaaag ctggcgcgcg tcacctggat tctctgaggt aatggagttc    42060
atagactcag taatcatcga acagaaatat cagcttgccg cgtccaacct catcaatgcc    42120
ggatttgtag gcaaagacat tggcatcgac aaggcggcag aagtcaatgt gagtaatgtt    42180
gtgaatgaca cgcaaaccat agaggatgcc gtgaaaagcg tactggataa gatttgataa    42240
aatctgacta tgtggataaa ataacccta acaattaatg tttaggggtt tttgctatgt    42300
ctaacaagat attgatttgg gaagatctga caccaaagga aaaggcggta ataaaggtga    42360
tgagcgaaag gtcgtttagt gactttatgc gcatatggtt cgcgctgata caggctcaga    42420
agtttagatc taactggcac ttcacttacc tttgctggaa ggttgagcag atcattaagg    42480
gtgagataca gaacatcata ttcaatatca ctccaggttc cggtaaaact gagatatttt    42540
ctatacacat gccagtttac ggaatgtttc acagtggcaa gataagaaat ctaaacctt    42600 cattctctga cagtttggtt aaggataacg ggattaggac gcgcgagata ttgggatctg    42660
atgagttcca ggaattatgg ccttgtaaga tggcaaaggc ttcaggagga gacattacag    42720
cgctaaacag taatgacaag gcgtggctga cgttaacatc tcgagccata ggtggtcagg    42780
taactggtaa gcgtggcggg tatatggacg atggattcac tggcatgttg acgcttgatg    42840
accctgagaa accgaaagat ttatactcag cagtaaaaag gaaggctggt cacacgctat    42900
taaagaatac cgttcgatct cgaaggatga acgacaagac gccgtgcgtt gttgtgcagc    42960
agcgactcca tgtgaatgat gccacatggt tcctgatgaa tggcggcatg ggtggcatga    43020
agtttgagca ggtaatcatt ccggcgctgg taaccgagga atacagagac acgcttcctg    43080
actggttgaa agaagagttt gaccgagatg ttttatcgtc cgagcctgtt gagattgatg    43140
gtattaagca ctattcattc tggccagcaa aggaaagtgc tcaaagttta ctagctctac    43200
gagaggctga cctttacacc tttgagtctc agtatcagca gaagcccatc gcgcttggcg    43260
gtaacgcgtt taagtcggac tggttccagt attacggaga cggcgaaaaa gccaatatgc    43320
caaaaccgga tcgcttcgaa tacctgttca ccactgcgga tacagcgcag aaagcagagg    43380
aaatacacga ctacagcgta tttgttttgt ggggcaagta taaggatcga gtatatttca    43440
tagacggcat tcgcggtaag tgggaagcgc cggaacttga aaagatggct cttaattttt    43500
acagcaactg cttcaagtgg gcgaaggaga acaagacttc actgcgcaag gtttacattg    43560
aagacaaggc gagcggcact ggcctgatcc agtcaatcaa caagaaacta ccgattgaca    43620
ttacgccagt tcagcgaaat acggataagg taactcgcgc aatggacgca gcaccaatca    43680
tgaaggcggg gcgttgtgta ttccctgaat ctcatgagat gctttctgac atggagattg    43740
aattggtgtc atttacgttt gatgattcat ctcctcatga tgacatttgc gataacgtat    43800
```

```
ttgatgctgt aaactttgag atgaacatgc tggatgatcc agtgtctaga atgaaacgtt    43860
tagccggatt aagtaggggg atgtaatgca gaatgcaaga agcgatattt atgacatagc    43920
caagaattat ctaacgtatg atggagttta tgttaggtgg atgatcaaga ttaaaaagag    43980
taaattctac cctggtgaca tagcgggaac acttgatgct gatggttatg tgaggataac    44040
gataggtggc gtatcgcttc ttgctcacag attcgcatgg gaattcgata atggagatat    44100
ccctgatggg atgcagatag atcacaaaaa tcacataagg aacgacaata ggagggaaa     44160 tttaagggtt gttacccata aggataacgg tagaaacaca agaagtcag taaggaataa    44220 aagcgggtgt gtaggtgttt actggtatga ttcaagatcc aagtggtggg ctttcatagg    44280
taactcaggg aaaggagaga ggaagtcatt gggatactac tatgattggt tcgatgcagt    44340
ttgcgcaagg aagtctgcgg agttcgcttt gggctatcat gaaaatcatg gtaagtcgga    44400
agtcaaataa tgtataatgg ctaggctaac aacctagcct tttttattgg gagaaaaaca    44460
gatgagtaaa aaaagcgtta agaccgactc ttacaacaag acgtttaagg gtgaaggtac    44520
ggcaggcggc gcgcttgcat cgctatacga tcagatgtat gtgacgcagt tttacattga    44580
tgatcctatg gctaagaaaa ttgtcgatgt tattccagag gaaatggttt tccctgggtt    44640
cggcctggac ggggtgaagg atgagaaggc gttcaaatct ttgtgggatg gcatgaagct    44700
gaacaagcag attgtcgagg cgttctcatg ggagaggctt tatggtggtt ccgctatcgt    44760
tgccgtcgtc cgtgacaacc gactcctgac atcaccaatc aaggaaggtg cgcagcttga    44820
atcaatccgc gtctacgaga aagagcagat ccgcatcaag gaccgcgaga agaacgcacg    44880
taatcctcgc tatggtatgc cgaagattta caccattaac cctggcggca gcataccgga    44940
atacgacgtc cactacacgc gaatctatgt taacggcggc gagcgattgc ctaactcaat    45000
tcgtgcgcaa aataacgaat ggggcgcatc ggtgttgagc aagggattga ttgatgccat    45060
tttggactac aactactgcg aagaacttgc cacacagcta ttgcgccgta agcagcaggg    45120
cgtatggaaa gctaaagggt tggcggattt gtgcgacgat gacgaaggtc gttacgcagc    45180
acggcttcga cttgcgcagg ttgatgataa cagcggcgta ggaaggacta ttggcattga    45240
tgccaccgac gaagaatacg acgttcttaa ctctgacatt ggcggcgttg atgctttctt    45300
ggataagaaa atggaccgca tcgtgaacta ctctggcatt catgagatta tcctcaagaa    45360
taagaacgta ggcggcgtgt cagcgagtca gaatacagcg cttgagactt tctataagat    45420
gattgaccgc aagcgtaacg agtattacag acattttctg gagtggttgc ttcctatgct    45480
tattcaggag gaggaatggt caatccgctt tgagccgcta tcaatgccaa gcagaaaaga    45540
gcaatccgag acgttgaaga ataacgttga atcgctttca agctgttggg ctgagcaggt    45600
tattgaccgt gacgaagcgc gtgatacact tgaggcaatc gcagacttta tcaagatcca    45660
aggcccagcg ccggagcttg aagaaatcga accaactaac ccgcaggtga caacgagga    45720 ataatcatga aggttaacgg cattgtaaat caatggagtt accccgaagc aagcgagcgg    45780
cagcttagcc gctcattgtc aaccttcgca ggcgagatgg caaagaaagc cagatcgctt    45840
actggcggga tgagattcga cgcttcggac gaagaaatca atgatgcaga ggatgagcta    45900
gaggaatacg ctgccggact gatcgcagca attgttgcca cacttccggc gctggccttg    45960
accatctaca agttcaactc aaggcaattc ctcaacgtgg caaagaaagc tggtggcgga    46020
aagaatcagt ctgtgatctt gcttggcgcg cttggtgcta atggtaatga gtcatggtat    46080
cgcgagaaat catcgcaatg gcgcggctct gctgaggcga gtattctaaa gctatcgaac    46140
```

```
gacattatct ctgactggtc gcaaaaccta cgcgtagaaa acgtgcgcaa taaaaccagt    46200
cagcagattg atgaagtttt aaagcagcgt tacaaggtgt atactggctg gaccgttaat    46260
cgctcacgtg gaatcgtgtc cacatggaac agcgtactga tgcgccagcg acttgatgat    46320
gctggagtaa ctcactattt ctggcatggt aaactggacg aacgcgagcg attgcagcac    46380
gtaaaatggg aaggtaaacg tattgagatc tcaagtgacc atccgttccc tggtgagcct    46440
tacggctgcc gatgctgggc cgtgccatca tttgatagca gtgggaatca actatgaatt    46500
tcaatgatta tttttatcat atagagaaag atctcatctg gaaaaatccg acatcgagaa    46560
gggttaaggc tggcgacgtt gctggttgga tggatgaaga tggatatatt tacgttagga    46620
tcatggggag gctaactccg gcacataggg taatatggga gatgcataac ggtgaaatac    46680
ccaaaggaat tgaaattgac catataaatc atatcagaga tgataacagg atagagaacc    46740
taagactcgt aaccaggcaa gagaattgca aaaacgtatc cataagcaag tcaaacaaga    46800
gcggagtttt cggggttagc tggtgtaaga gaacggggaa atggtttgct tcaataaggg    46860
tgaacaaaaa ggagaaattc cttggtagat acgatagaaa agatgacgca atatctgcaa    46920
gaaaggctgc agagtctgta tatgaatttc ataaaaatca cgggagtaaa aaatgacaac    46980
caagcaaaga tacgatagcg tgcaactgaa agcgcgcttt gactcaaacg gattcatgca    47040
cgatgagcca atcattgcac gaatcggcat tcaggaatat atgcgtgccg atggaacaat    47100
gcagcgtgag ttccgaccag ccaacgaagt gttcaaggcc gaggcgatgg aactgtttcg    47160
cggtatgcct atcgtagagg gccaccagga agtaagcaca gacaacgcgc gaaagattgt    47220
tgttggctca ctatctggcg ctggtcgccg tgacggcatc ggcttaaagt gtccgatcgt    47280
aatccacgac aaggaatcca ttgaatccgc caagcgtggc gacgccgcag aattgtcggt    47340
tggttacaag actaatgaca ttcatcgcga aggttgggga acgtcaata ctggcgagta    47400 tgttttcaag gatgacgcgg aagggatgga ggcacaattc cctaacggaa ctgtcatgac    47460
tgacgaatgg gaagagttcg acgtactgca aacgaacatc gtgcctaacc acgttgccaa    47520
ggtaaagcac gggcgcgcag gtattgccag attaaacctt gacggctcag aagaaattaa    47580
atatgatgag catgttcaat taaccaatga ggaaagtaac atgaccgtaa aaatcaaaat    47640
tgattcagca gaagtggaag tgtccaaaga cgtagctgac cacatcggca aactgcaaaa    47700
cgcagcagaa caagctggtg ctaaagttga cggcctgcaa gctgagcgcg acgcgctgca    47760
agcaaaggtt gacggcattc cggcacagat tgaagccgct ctggcagatg caaaagagaa    47820
agctgacgcg ctgggcgctg ttctcacttt cgcttccggc ctcggcatca agtgtgatgg    47880
cctggacgag aaagctatta agctggcagt cattgacgaa gttctcggca ttgacgcaaa    47940
agaaaaatcc gacgcataca tcaatcagtc ttatgaaatc gctcgcgatt ctgataaaat    48000
ggcggctcaa cgcatcaaag tgcacggcga caaagccgac ggcgctcagg gcgacaaaga    48060
taatgacgcg attcctgatc cacaggctcg cttccgtaag taataaaatg gcggtctaaa    48120
ggacgcttaa tctctaagtg aaaaaggaaa aatatcatgg cactaatcaa agcatcttat    48180
acggttaacc gttcaaaagc atatgcaggc ctgctggctg acacttctct ctacaacgtt    48240
gatggcgctt gtgcagcggc taagaaaatt aaggttggcg tggtagtcgc cctcgaccct    48300
accggaaagg ttgttgatgg tcacaaagtc gtaactgaca ccatctcggc agaaactccg    48360
aacctggtgg gcgtagccat catgtctcac gcatactctc cggatggtgc ttatgacgaa    48420
ggttctgcaa tcaacgtact gacaaatggt cgagcatggg tgctgtgtgc taaagacctg    48480
ccagaagtga acaaagagtt caataagcag gtattcttga ccacttcggg tactgtggcg    48540
```

```
gcaactggca ttggcactgt ttacaccacc accggcgagt ggctaaagac tgatgatgag  48600
aacttcgaca ttatcaaaat ccaggttact caagctcaat tccagcttcc ggcaagtccg  48660
gcagcttaat atctgaacca taatagggag ccgaaaggct cctttttat tgccagagag  48720 cgacataatc gcttaacata aaaagctgtt gaccgtttaa caaaaaatgc tattatagag  48780
ccgtgaactt aatcacggct ttctaacaaa caaggaaaa caaattatga ctatgaaact  48840
cgacgctttc gagcagaaca tgattactaa cggtatgcgc cagcttggcg taagcggcaa  48900
caaagccgac cagcttggca tctggactgt caaacagatg actcagttgc ttaagcgcca  48960
gtatgaagcg gcttaccctg aaacctacgc gctggctctg ttccctgtca ctactgagat  49020
tagcccgacc gctaacctgt tcgaatatct caagtttgac ggcgtgacca tggcgaagat  49080
tatcgctgac tacaccgacg acctgccaac tgttgacgct actcacagtc tggaatctgg  49140
tcgagttcac cgcctcggta acgcgtggct gatctctatc gacgagatta aaactggtgc  49200
ggcacttggt tcaagcctgt cagatcgtaa agcgactctg gcacgcgaag gtcacgaaac  49260
tctggttaac cagttggtct tcaaagggtc caagcctcac aagatcatct ctgttttcga  49320
ccatccgaac atcacccgtg tgacttctgt tgctggtgcg tggggcgatg cagagaaagc  49380
aagcgaagaa ctgaccgacc tgatcgagaa gatggaaacc ctgaccaatg gtcagcacaa  49440
gatcaccgac atcgttatcc cgccgtcaca gcgtaaattg ctcgctaagc gtatgccgga  49500
aaccacgatg agttatctgg actggttcaa gtctcagaac ggtggcatca ccatctcttc  49560
catctctgaa ctggaagaca tcgacggcgc aggcactaaa gctgttctgg cgtatgaga  49619
```

BACTERIOPHAGE AND ANTIBACTERIAL COMPOSITION COMPRISING THE SAME

TECHNICAL FIELD

The present invention relates to a novel bacteriophage having a specific bactericidal activity against Enterotoxigenic *Escherichia coli* (ETEC), and an antibacterial composition comprising the same. In addition, the present invention relates to a method of preventing or treating animal diseases using the novel bacteriophage or the antibacterial composition.

BACKGROUND ART

*Escherichia coli* (hereinafter referred to as '*E. coli*' is a Gram-negative, short rod-shaped bacterium belonging to the genus *Escherichia* and the family Enterobacteriaceae, and is one of the normal flora existing in the intestines of various animals including mammals. It was known that most of the strains of *E. coli* are non-pathogenic and may cause opportunistic infections, but some highly pathogenic strains cause diverse intestinal diseases and sepsis in animals including humans.

An example of *E. coli* may include enterotoxigenic *E. coil* (ETEC), enteropathogenic *E. coil* (EPEC), enterohemorrhagic *E. coil* (EHEC), enteroaggregative *E. coil* (EAEC), enteroinvacive *E. coil* (EIEC), necrotoxigenic *E. coil* (NTEC), or the like. It is known that among them, particularly, the ETEC generates infectious disease associated with *E. coli* in swine.

Currently, as a large number of swine are collectively bred in a pork industry, colibacillosis has been in the spotlight as a most frequent and troublesome disease (Non-Patent Document 1). Recently, occurrence of swine colibacillosis has increased in Korea, which has caused growth retardation and death of young swine due to diarrhea, resulting in tremendous economic losses to farmers (Non-Patent Document 2).

In order to prevent and treat colibacillosis in swine, many antibiotics have been administered to swine in the prior art, but when antibiotics has been misused or overused, the misused or overused antibiotics may give rise to drug resistance and remain in bodies of the swine. Therefore, currently, the use of antibiotics has been restricted around the world (Non-Patent Document 3).

Meanwhile, bacteriophage is a specialized type of virus that infects and destroys only bacteria, and can self-replicate only inside host bacteria. The bacteriophage has strong host specificity as compared to antibiotics, and recently, a problem of emergence of strain resistant against antibiotics has been serious, such that an interest in practical use of the bacteriophage has increased (Non-Patent Documents 4 and 5).

Therefore, research into the bacteriophage has been actively conducted in various countries around the world, and in addition to a patent application for bacteriophage, an attempt to acquire Food and Drug Administration (FDA) approval for a composition containing the bacteriophage has been gradually increased.

As the prior art for the bacteriophage, 7 kinds of bacteriophages for controlling *E. coli* 0157:H have been disclosed in Patent Document 1, and a bacteriophage having killing activity specific to *Staphylococcus aureus* has been disclosed in Patent Document 2. Further, lytic protein derived from a bacteriophage specifically destroying a peptidoglycan structure of bacterial cell membrane, and bacteria lysates by the lytic protein have been disclosed in Patent Document 3.

However, in spite of presence of the following prior arts, a technology associated with the bacteriophage for preventing and/or treating infectious diseases by the ETEC that are a still important problem in an livestock industry including the pork industry is still insufficient, such that a bacteriophage and a technology associated with the bacteriophage should be developed.

PRIOR ART DOCUMENTS

Patent Documents (Patent Document 1) U.S. Pat. No. 6,485,902
(Patent Document 2) Korea Patent No. 10-0910961 B1
(Patent Document 3) Korean Patent Application Publication No. 10-2009-0021475 A

Non-Patent Document (Non-Patent Document 1) Young Il Park, Swine production science, Sunjin Publishing group, 353-359, 1998
(Non-Patent Document 2) Eu Chul Hong, master's thesis, Dankook University, Addition Effect of Egg Yolk in Early Weaned Piglets, 2001
(Non-Patent Document 3) Mason H S et al., Trends in Biotech, 13:388-392, 1995
(Non Patent Document 4) Cislo M, et al., Arch. Immunol. Ther. Exp. 2:175-183, 1987
(Non Patent Document 5) Sung Hun Kim et al, Bacteriophage, novel alternative antibiotics, BioWave Vol. 7 No. 15, 2005, BRIC

DISCLOSURE

Technical Problem

The present inventors conducted studies in order to solve problems such as resistant bacteria occurring upon the use of antibiotics, antibiotics remaining in meat, and the like, and efficiently prevent and treat infectious diseases by *E. coli*, and as a result, the present inventors isolated new bacteriophage ΦCJ19 (KCCM11361P) having a specific bactericidal activity against ETEC from the nature.

In addition, the present inventors identified morphological, biochemical, and genetic characteristics of the novel bacteriophage and confirmed that the bacteriophage had excellent acid resistance, heat resistance, and the like, thereby developing an antibiotic, a disinfectant, a feed additive, and other compositions using the novel bacteriophage.

Further, the present inventors developed a composition for preventing or treating infectious diseases by *E. coli*, and a method of preventing or treating the disease using the composition.

The present invention provides a novel bacteriophage ΦCJ19 (KCCM11361P) having a specific bactericidal activity against ETEC.

In addition, the present invention provides a composition for preventing and/or treating infectious diseases by ETEC containing the bacteriophage ΦCJ19 (KCCM11361P) as an active ingredient.

Further, the present invention provides an antibiotic, a feed additive, a drinking water additive, a disinfectant, or a cleaner containing the bacteriophage ΦCJ19 (KCCM11361P) as an active ingredient.

Furthermore, the present invention provides a method of preventing and/or treating infectious diseases by ETEC in animals except for humans using the bacteriophage ΦCJ19 (KCCM11361P) or a composition containing the bacteriophage ΦCJ19 (KCCM11361P) as an active ingredient.

Technical Solution

According to an exemplary embodiment of the present invention, there is provided a novel bacteriophage ΦCJ19 (KCCM11361P) having a specific bactericidal activity against enterotoxigenic *Escherichia coli* (ETEC).

According to another exemplary embodiment of the present invention, there is provided a composition for preventing or treating an infectious disease caused by ETEC, containing the bacteriophage ΦCJ19 (KCCM11361P) as described above as an active ingredient.

According to another exemplary embodiment of the present invention, there are provided an antibiotic, a feed additive, a drinking water additive, a disinfectant, or a cleaner containing the bacteriophage ΦCJ19 (KCCM11361P) as described above as an active ingredient.

According to another exemplary embodiment of the present invention, there is provided a method of preventing or treating an infectious disease caused by ETEC, comprising administering the bacteriophage ΦCJ19 (KCCM11361P), or the composition containing the bacteriophage ΦCJ19 as described above to animals except for humans.

Advantageous Effects

The bacteriophage ΦCJ19 (KCCM11361P) according to the present invention has an effect of specifically killing enterotoxigenic *Escherichia coli* (ETEC).

In addition, the bacteriophage ΦCJ19 (KCCM11361P) according to the present invention has excellent acid resistance and heat resistance, such that the bacteriophage ΦCJ19 (KCCM11361P) may be used as a material for preventing or treating infectious diseases by ETEC in various temperature or pH ranges and utilized as an antibiotic, a feed additive, a drinking water additive, a disinfectant, a cleaner, or the like.

Further, according to the present invention, infectious diseases by ETEC may be prevented or treated by administering the bacteriophage ΦCJ19 (KCCM11361P) or a composition containing the bacteriophage ΦCJ19 (KCCM11361P) as an active ingredient to animals except for humans.

BEST MODE

Figure 1:
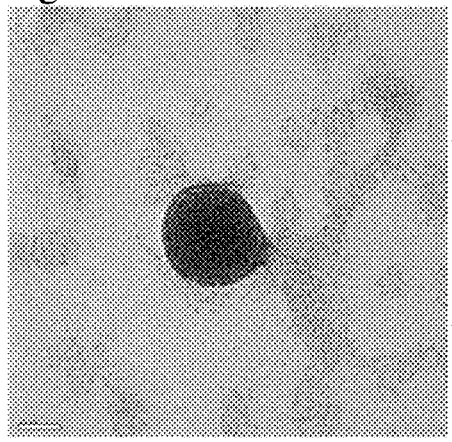
FIG. 1 is an electron microscope photograph of a novel bacteriophage ΦCJ19 (KCCM11361P, hereinafter, referred to as 'ΦCJ19').

Hereinafter, the present invention will be described in detail. Since contents that are not described in the present specification may be sufficiently recognized and inferred by those skilled in the art or similar art, a description thereof will be omitted.

In detail, in an embodiment, the present invention provides a novel bacteriophage ΦCJ19 (KCCM11361P) having a specific bactericidal activity against enterotoxigenic *Escherichia coli* (ETEC).

The ETEC, which is a Gram-negative, rod-shaped bacterium, is an aerobic or facultative anaerobic bacterium decomposing lactose or fructose to produce acid and gas. The ETEC well grows in a general medium and may grow at about 7 to 48° C., and an optimal growth temperature is about 35 to 37° C. In addition, the ETEC may grow in a pH range of 4.5 to 9.

Since ETEC produces toxin similar to that of *Vibrio cholerae*, in the case of infection of ETEC, symptoms similar to those of cholera are exhibited. The produced toxins are divided into two kinds, that is, a heat-labile enterotoxin (LT) and heat-stable enterotoxin (ST). The heat-labile enterotoxin means an enterotoxin losing its activity in the case of heating at 60° C. for 10 minutes, and the heat-stable enterotoxin means an enterotoxin that does not lose its activity even in the case of heating at 100° C. for 30 minutes.

In the case in which a concentration of ETEC arrives at $10^7$ cfu (colony formation unit) to $10^8$ cfu per a unit volume (1 ml) of serous fluid while ETEC proliferates in an upper portion of intestine, ETEC causes infectious diseases by *E. coli* such as colibacillosis.

A bacteriophage is a bacteria-specific virus infecting specific bacteria to suppress and inhibit growth of the bacteria and means a virus including single or double stranded deoxyribonucleic acid (DNA) or ribonucleic acid (RNA) as a genetic material.

The bacteriophage ΦCJ19 according to the present invention, which is a bacteriophage species-selectively infecting ETEC, has a structure of an isometric capsid but a tail is not observed (FIG. 1), and morphologically belongs to Podoviridae.

The bacteriophage ΦCJ19, which was a bacteriophage newly isolated by the present inventors, was deposited at Korean Culture Center of Microorganisms (361-221, Hongjedong, Seodamun-gu, Seoul, Korea) as a deposition number KCCM11361P on Jan. 30, 2013.

In another embodiment, the present invention provides a composition for preventing or treating infectious diseases by ETEC containing the bacteriophage ΦCJ19 as an active ingredient.

Since the bacteriophage ΦCJ19 has an antibacterial activity capable of specifically killing ETEC, the bacteriophage ΦCJ19 may be used to prevent or treat diseases generated by infection of ETEC. An example of the infectious disease caused by ETEC that may be treated using the bacteriophage ΦCJ19 may include preferably colibacillosis, more preferably colibacillosis in swine, but is not limited thereto.

The term "colibacillosis" as used herein means a disease caused by infection of an animal with pathogenic *E. coli*, and shows symptoms such as sepsis, diarrhea (neonatal diarrhea and post-weaning diarrhea), toxemia (edema and cerebrospinal angiopathy), or the like. Among them, sepsis is an acute systemic infection that frequently occurs in 2 to 3 days after birth and has a high mortality rate. Diarrhea is the most common outcome of gastrointestinal tract infections that occur during the lactation period within 1-2 weeks after birth and immediately after the weaning period, and causes death or growth retardation. Toxemia mainly occurs in 8-12 weekold piglets after the weaning period, and is frequently accompanied by edema and neurologic signs, followed by sudden death.

The term "prevention" as used herein refers to all actions of providing the bacteriophage ΦCJ19 and/or the composition containing the bacteriophage ΦCJ19 as the active ingredient to animals except for humans to suppress the corresponding disease or retard disease occurring.

The term "treatment" as used herein refers to all actions of providing the bacteriophage ΦCJ19 and/or the composition containing the bacteriophage ΦCJ19 as the active ingredient to animals except for humans to thereby allow the symptom of the corresponding disease caused by infection to get better or be alleviated.

The composition for preventing or treating the infectious disease caused by ETEC according to the present invention may contain the bacteriophage ΦCJ19 in an amount of preferably $5 \times 10^2$ to $5 \times 10^{12}$ pfu/ml, more preferably, $1 \times 10^6$ to $1 \times 10^{10}$ pfu/ml.

The composition for preventing or treating the infectious disease caused by ETEC according to the present invention may further contain a pharmaceutically acceptable carrier and be formulated together with the carrier to thereby be provided as food, a feed additive, a drinking water additive, and the like. The term "pharmaceutically acceptable carrier" as used herein means a carrier or a diluent that does not stimulate living organism nor inhibit biological activity and properties of an administered compound.

A kind of carrier usable in the present invention is not particularly limited, and any carrier may be used as long as it is generally used in the art and is pharmaceutically acceptable. As a non-restrictive example of the carrier, there are normal saline, sterile water, buffered saline, Ringer's solution, an albumin injection solution, a dextrose solution, a maltodextrin solution, glycerol, ethanol, and the like. One or a mixture of at least two of these carriers may be used.

In addition, if necessary, another general additive such as an antioxidant, a buffer, a bacteriostatic agent, and/or the like, may be further added and used, and the composition may be formulated into an injection formulation such as an aqueous solution, suspension, emulsion, or the like, pills, capsules, granules, tablets, or the like by additionally adding a diluent, a dispersant, a surfactant, a binder, a lubricant, and/or the like, and then used.

An administration method of the composition for preventing or treating infectious diseases by ETEC is not particularly limited, and any method generally used in the art may be used. As a non-restrictive example of the administration method, the composition may be orally or parenterally administered.

As a non-restrictive example of the formulation for oral administration, there are troches, lozenge, tablets, aqueous suspensions, oily suspensions, prepared powder, granules, emulsions, hard capsules, soft capsules, syrups, elixirs, or the like.

In order to formulate the composition according to the present invention into a formulation such as a tablet, a capsule, or the like, the formulation may further contain a binder such as lactose, saccharose, sorbitol, mannitol, starch, amylopectin, cellulose, gelatin; an excipient such as dicalcium phosphate, or the like; a disintegrant such as corn starch, sweet potato starch, or the like; a lubricant such as magnesium stearate, calcium stearate, sodium stearyl fumarate, polyethylene glycol wax, or the like. In the case of capsule formulation, the formulation may additionally contain a liquid carrier such as fatty oil in addition to the above-mentioned materials.

As a parenteral administration method, an intravenous administration method, an intraperitoneal administration method, an intramuscular administration method, a subcutaneous administration method, a local administration method, or the like, may be used. In addition, a method of applying or spraying the composition onto a disease site may also be used, but the present invention is not limited thereto.

An example of the formulation for parenteral administration may include injection formulations for subcutaneous injection, intravenous injection, intramuscular injection, or the like; suppository formulations; spray formulations such as aerosol formulations capable of being inhaled through respiratory system, or the like, but the present invention is not limited thereto. In order to formulate the composition into the injection formulation, the composition according to the present invention may be mixed with a stabilizer or a buffer in water to thereby prepare a solution or suspension, and then, the prepared solution or suspension may be formulated in a unit dose for an ampoule or vial. In the case of formulating the composition into the spray formulation such as the aerosol formulation, or the like, a propellant, or the like, may be mixed together with an additive so that a water-dispersed condensate or wet powder is dispersed.

A suitable application, spray, or administration dose of the composition for preventing or treating infectious diseases by ETEC may be variously determined depending on factors such as age, weight, sex, degree of symptom of disease, a kind of food, excretion rate of administration target animals, or the like, as well as a method of formulating the composition, an administration method, an administration time and/or route. Generally, a veterinarian having ordinary skill in the art may easily determine and prescribe an effective dose for the desired treatment.

In another general aspect, the present invention may provide an antibiotic containing the bacteriophage ΦCJ19 as an active ingredient.

The term 'antibiotic' as used herein means an agent capable of being provided to animals including humans in a drug form to thereby kill bacteria, and corresponds to a concept collectively indicating a preservative, a disinfectant, and an antibacterial agent.

The antibiotic containing the bacteriophage ΦCJ19 according to the present invention as the active ingredient may have high specificity to ETEC as compared to an antibiotic according to the prior art to thereby not kill beneficial bacteria but kill specific pathogenic bacteria, and does not induce drug resistance, such that the antibiotic according to the present invention may be provided as a novel antibiotic having an elongated lifespan as compared to the antibiotic according to the prior art.

In another general aspect, the present invention may provide a feed additive and a drinking water additive containing the bacteriophage ΦCJ19 as an active ingredient.

The feed additive and the drinking water additive according to the present invention may be used in a manner in which the bacteriophage ΦCJ19 or the composition containing the bacteriophage ΦCJ19 is individually prepared in a feed additive or drinking water additive form and then mixed with a feed or drinking water, or in a manner in which the bacteriophage ΦCJ19 or the composition containing the bacteriophage ΦCJ19 is directly added at the time of preparing the feed or the drinking water.

The bacteriophage ΦCJ19 or the composition containing the bacteriophage ΦCJ19 used as the feed additive or drinking water additive according to the present invention may be in a liquid state or dried state, and preferably, in a dried powder form.

A drying method for preparing the feed additive and the drinking water additive according to the present invention in the dried powder form is not particularly limited, but a method generally used in the art may be used. As a non-restrictive example of the drying method, there is a natural air drying method, natural drying method, a spray drying method, a freeze-drying method, or the like. One method of these methods may be used alone or at least two methods may be used together with each other.

Another non-pathogenic microbe may be additionally added to the feed additive or drinking water additive. A non-restrictive example of the microbe capable of being added may be selected from a group consisting of *bacillus* sp. capable of producing protease, lipase, and/or sugar converting enzyme such as *bacillus subtilis*, or the like; *Lactobacillus* sp. having physiological activity and degradation activity for an organic material under anaerobic conditions such as cow's stomach; mold fungi having effects of increasing a weight of domestic animal, a milk yield, and digestibility of the feed such as *Aspergillus oryzae*, or the like; and yeasts such as *Saccharomyces cerevisiae*, or the like. One or a mixture of at least two of these microbes may be used.

The feed additive or the drinking water additive containing the bacteriophage ΦCJ19 according to the present invention as the active ingredient may further contain other additives, as needed. As a non-restrictive example of the usable additive, there are a binder, an emulsifier, a preservative, and the like, which are added in order to prevent quality of the feed or driving water from being deteriorated; amino acids, vitamins, enzymes, probiotics, flavoring agents, non-protein nitrogen compounds, silicates, buffers, coloring agents, extractants, oligosaccharides, and the like, which are added in order to increase utility of the feed or drinking water. Otherwise, the additive may further include a feed mixing agent, or the like. One or a mixture of at least two of these additives may be used.

The feed additive may be contained at a content of 0.05 to 10, more preferably 0.1 to 2 parts by weight based on 100 parts by weight of the feed. The drinking water additive may be contained at a content of 0.0001 to 0.01, more preferably 0.001 to 0.005 parts by weight based on 100 parts by weight of the drinking water. The activity of the bacteriophage ΦCJ19 against ETEC may be sufficiently exhibited in the above-mentioned range.

In another general aspect, the present invention provides a feed or drinking water prepared by adding a feed additive or a drinking water additive containing the bacteriophage ΦCJ19 as an active ingredient or directly adding the bacteriophage ΦCJ19.

The feed used in the present invention is not particularly limited, but any feed generally used in the art may be used. A non-restrictive example of the feed may include plant feeds such as grains, roots and fruit, food processing byproducts, algaes, fibers, pharmaceutical byproducts, fats, starches, cucurbitaceous, or grain byproducts; and animal feeds such as proteins, inorganic materials, fats, minerals, single cell proteins, animal planktons, or foods. One or a mixture of at least two of these feeds may be used.

The drinking water used in the present invention is not particularly limited, but any drinking water generally used in the present invention may be used.

In another general aspect, the present invention may provide a disinfectant or a cleaner containing the bacteriophage ΦCJ19 as an active ingredient. A formulation of the disinfectant or cleaner is not particularly limited, but the disinfectant or cleaner may be formulated into any formulation known in the art.

The disinfectant may be sprayed in order to remove ETEC onto a region in which animals live, a slaughterhouse, a mortality generation area, a cooking place or cooking equipment, or the like, but the present invention is not limited thereto.

The cleaner may be used to wash skin's surfaces or each of the sites of bodies of animals exposed or to be exposed to ETEC, but the present invention is not limited thereto.

In another general aspect, the present invention provides a method of preventing or treating infectious diseases by using the bacteriophage ΦCJ19 or the composition comprising the bacteriophage ΦCJ19 as an active ingredient.

In detail, the method of preventing or treating infectious diseases according to the present invention may include administering the bacteriophage ΦCJ19 or the composition containing the bacteriophage ΦCJ19 as the active ingredient to targets infected by ETEC or being at risk of infection of ETEC except for humans in a pharmaceutically effective dose.

It will be apparent to those skilled in the art that when the pharmaceutical composition is administered to patient, the suitable total daily dose may be determined by an attending physician or veterinarian within the scope of sound medical judgement.

A specific pharmaceutically effective dose of the bacteriophage ΦCJ19 or the composition containing the bacteriophage ΦCJ19 as the active ingredient for a specific animal may be determined by considering an administration time and an administration route of the bacteriophage ΦCJ19 or the composition containing the bacteriophage ΦCJ19, a secretion rate of the composition, a therapy duration period, or the like, in addition to a kind and a degree of the desired response, an age, a weight, a general healthy state, sex, or diet of the corresponding individual. In addition, the pharmaceutically effective dose may be variously changed according to various factors such as ingredients of drugs or other compositions simultaneously or separately used and similar factors well known in a medical field.

The bacteriophage ΦCJ19 according to the present invention or the composition containing the bacteriophage ΦCJ19 as the active ingredient may be administered as a pharmaceutical form (nasal spray) to animals or administered in a method of directly added to a feed or drinking water of the animals and then feeding the feed or drinking water. In addition, the bacteriophage ΦCJ19 or the composition containing the same may be mixed in a feed or drinking water in a form of a feed additive or drinking water additive and then administered.

The administration route and administration method of the bacteriophage ΦCJ19 according to the present invention or the composition containing the bacteriophage ΦCJ19 as the active ingredient are not particularly limited, but any administration route and administration method may be used as long as the bacteriophage ΦCJ19 or the composition containing the same may arrive at the corresponding target tissue. That is, the bacteriophage ΦCJ19 or the composition containing the bacteriophage ΦCJ19 as the active ingredient may be administered through various oral or parenteral routes. As a non-restrictive example of the administration route, oral, rectal, local, intravenous, intraperitoneal, intramuscular, intraarterial, subcutaneous, and nasal administration, inhalation, or the like, may be performed.

Hereinafter, the present invention will be described in detail through the Examples. However, these Examples are only to illustrate the present invention, and a scope of the present invention is not limited to these Examples.

Example 1

Isolation of Bacteriophage Infecting ETEC

Examples 1-1

Screening of Bacteriophage and Isolation of Single Bacteriophage

After 50 ml of a sample obtained from pig feces and environmental samples of Samwhaw Gps. Breeding Agri. in Gwangcheon area, Hong seong-gun, Chungchong Province was centrifuged at 4,000 rpm for 10 minutes, the supernatant was filtered with a 0.45 μm filter to prepare a sample solution, and then a soft agar overlay method was performed using the prepared sample solution. The soft agar overlay method is a method of observing a lysis action of bacteriophage using host cells growing in top agar (attached onto a solid medium using 0.7% agar).

In detail, 18 ml of the sample filtrates was mixed with 150 μl of a shake culture solution ($OD_{600}$=2) of ETEC (SNUJG280) obtained from College of Veterinary Medicine, Seoul National University and 2 ml of 10× Luria Bertani (LB) medium (tryptone 10 g/l, yeast extract 5 g/l, and NaCl 10 g/l) and cultured at 30° C. for 18 hours. Then, the culture solution was centrifuged at 4,000 rpm for 10 minutes, and the supernatant was filtered with a 0.45 μm filter. Then, after a mixed solution of 3 ml of 0.7% (w/v) agar and 150 μl of the shake culture solution ($OD_{600}$=2) of ETEC (SNUJG280) was poured and hardened onto a LB plate medium, 10 μl of the sample solution was dropped thereon, followed by culturing at 30° C. for 18 hours. Then, it was confirmed that a plaque was formed.

Since it is known that one kind of bacteriophage is present in a single plaque, separation of a single bacteriophage from the formed plaque was attempted. In detail, the plaque was added to 400 μl of a SM solution (NaCl (5.8 g/l), $MgSO_4 7H_2O$ (2 g/l), 1M Tris-Cl (pH 7.5, 50 ml)) and left at room temperature for 4 hours, thereby obtaining a bacteriophage solution. Thereafter, 100 μl of the bacteriophage solution was mixed with 5 ml of 0.7% (w/v) agar and 150 μl of the shake culture solution ($OD_{600}$=2) of ETEC (SNUJG280), followed by performing the soft agar overlay method using a LB medium having a diameter of 150 m. The culturing was performed until ETEC was completely lysed. After the culturing was terminated, 5 ml of the SM solution was added to the LB plate medium and left at room temperature for 4 hours, thereby obtaining a bacteriophage solution.

After the solution was recovered and 1% (v/v) chloroform was added thereto, the mixture was mixed for 10 minutes, followed by centrifugation at 4,000 rpm for 10 minutes, thereby obtaining a supernatant. The obtained supernatant was filtered with a 0.45 μm filter, thereby obtaining a final sample.

Examples 1-2

Large-Scale Culture and Purification of Bacteriophage

The bacteriophage obtained in Example 1-1 was cultured at large scale using ETEC (SNUJG280), and then the bacteriophage was purified therefrom.

In detail, after ETEC (SNUJG280) was shake-cultured, and an aliquot of $1.5 \times 10^{10}$ cfu was centrifuged at 4,000 rpm for 10 minutes and then resuspended in 4 ml of the SM solution. The bacteriophage of $1.5 \times 10^6$ pfu was inoculated thereto (multiplicity of infection (MOI)=0.0001), and left at room temperature for 20 minutes. Thereafter, the solution was inoculated into 150 ml of the LB medium and cultured at 30° C. for 5 hours.

After the culturing was terminated, chloroform was added at an amount of 1% (v/v) of a final volume and stirred for 20 minutes. Then, restriction enzymes DNase I and RNase A were added so as to have a final concentration of 1 μg/ml, respectively, and the solution was left at 30° C. for 30 minutes. Then, NaCl and polyethylene glycol (PEG) were added so as to have final concentrations of 1M and 10% (w/v), respectively, and further left at 4° C. for 3 hours, followed by centrifugation at 4° C. and 12,000 rpm for 20 minutes, thereby obtaining precipitates.

The obtained precipitate was suspended in 5 ml of a SM solution and left at room temperature for 20 minutes. Then, 1 ml of chloroform was added thereto and stirred, followed by centrifugation at 4° C. and 4,000 rpm for 20 minutes, thereby obtaining a supernatant. Thereafter, the supernatant was filtered with a 0.45 μm filter, and ultracentrifugation (35,000 rpm, 1 hour, 4° C.) using a glycerol density gradient method (density: 40%, 5% glycerol) was performed, thereby purifying the bacteriophage.

The present inventor designated the bacteriophage obtained by extracting the sample from pig feces and having the specific bacteriocidal activity against ETEC as "Bacteriophage ΦCJ19" and deposited the bacteriophage at Korean Culture Center of Microorganisms (361-221, Hongjedong, Seodamun-gu, Seoul, Korea) as a deposition number KCCM11361P on Jan. 30, 2013.

Example 2

Examination of ΦCJ19 Infection on E. coli

In order to confirm whether or not the bacteriophage ΦCJ19 purified in Example 1 has a lytic activity on E. coli species other than ETEC (SNUJG280), cross infection with other E. coli species was performed.

In detail, 2 kinds of ETEC (SNUJG280 and CANR08 (obtained from University of Guelph in Canada)) strains and 12 kinds of non-pathogenic E. coli strains (MC4100, BL21 (DE3), Rosetta(DE3), 2616, 281, 1917, DH5a, GM2929, Tuner(DE3), W3110, K12G, and 0122ΔLT) were cultured, thereby obtaining culture solutions, respectively. Then, each of the culture solutions and the purified bacteriophage ΦCJ19 were used to perform the soft agar overlay method, and whether or not a plaque was formed was confirmed.

The results were shown in the following Table 1.

TABLE 1

| Serotype | strain | Plaque formation |
| --- | --- | --- |
| Non-pathogenic E. coli | MC4100 | o |
| | BL21(DE3) | o |
| | Rosetta(DE3) | o |
| | 2616 | x |
| | 281 | x |
| | 1917 | x |
| | DH5a | x |
| | GM2929 | o |
| | Turner | o |
| | W3110 | o |
| | K12G | x |
| | 0122(ΔLT) | o |
| ETEC | SNUJG280 | o |
| | CANR08 | o |

As shown in Table 1, it may be confirmed that the bacteriophage ΦCJ19 purified in Example 1 had the lytic activity on 7 kinds of non-pathogenic *E. coli* strains (MC4100, BL21(DE3), Rosetta(DE3), GM2929, Tuner (DE3), W3110, and 0122ΔLT) but did not have lytic activity on the residual 5 kinds of non-pathogenic *E. coli* strains (2616, 281, 1917, DH5a, and K12G) among the non-pathogenic *E. coli* strains.

Example 3

Morphology Observation of ΦCJ19

The bacteriophage ΦCJ19 purified in Example 1 was diluted in a 0.01% gelatin solution, and then fixed in a 2.5% glutaraldehyde solution. The fixed bacteriophage was dropped onto a carbon-coated mica plate (ca. 2.5×2.5 mm), adapted thereto for 10 minutes, and washed with sterile distilled water. A carbon film was mounted on a copper grid, stained with 2% uranyl acetate for 30 to 60 seconds, dried, and investigated using a transmission electron microscope (JEM-1011, 80 kV, magnification: ×120,000 to ×200,000) (FIG. 1).

FIG. 1 is an electron microscopy photograph of the bacteriophage ΦCJ19. It may be appreciated that the bacteriophage ΦCJ19 has an isometric capsid but does not have a tail, such that the bacteriophage ΦCJ19 morphologically belongs to Podoviridae.

Example 4

Genomic DNA Size Analysis of ΦCJ19

Genomic DNA was extracted from the bacteriophage ΦCJ19 purified in Example 1.

In detail, 20 mM ethylenediaminetetraacetic acid (EDTA), 50 μg/ml proteinase K, and 0.5% (w/v) sodium dodecyl sulfate (SDS) were added to a culture solution of the purified bacteriophage ΦCJ19 and left at 50° C. for 1 hour. An equal volume of phenol (pH 8.0) was added and stirred, followed by centrifugation at room temperature and 12,000 rpm for 10 minutes, thereby obtaining a supernatant.

The supernatant was mixed with an equal volume of PC (phenol:chloroform=1:1) and centrifuged at room temperature and 12,000 rpm for 10 minutes, thereby obtaining a supernatant. The supernatant was mixed with an equal volume of chloroform and centrifuged at room temperature and 12,000 rpm for 10 minutes, thereby obtaining a supernatant. The obtained supernatant was mixed with 10% (v/v) of 3M sodium acetate and then double volume of cold 95% ethanol, based on the total volume, and left at −20° C. for 1 hour. Subsequently, centrifugation was performed at 0° C. and 12,000 rpm for 10 minutes, and the precipitate was obtained by removing the supernatant. Then, 50 μl of Tris-EDTA (TE) buffer (pH 8.0) was added thereto to thereby dissolve the obtained precipitate. The extracted DNA was diluted 10 times, and a concentration was measured by measuring absorbance at $OD_{260}$.

Figure 2:
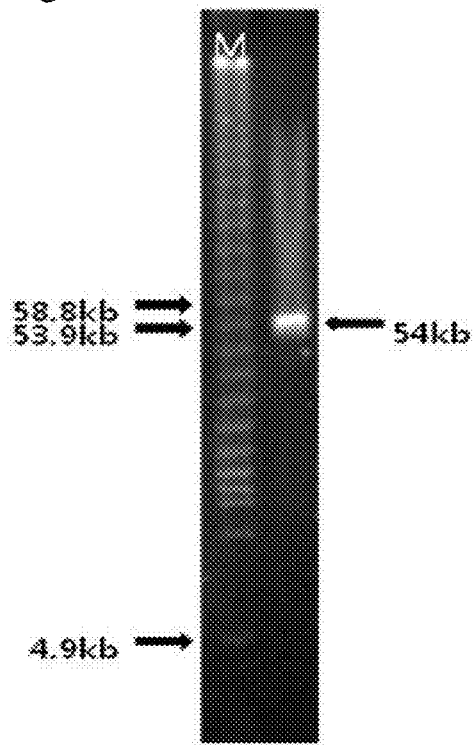
FIG. 2 shows a pulsed field gel electrophoresis (PFGE) result of the novel bacteriophage ΦCJ19.

Next, 1 μg of DNA was loaded onto 1% pulse-field gel electrophoresis (PFGE) agarose gel, and electrophoresis was performed at room temperature for 20 hours using a BIO-RAD PFGE system program 7 (size range: 25-100 kb; switch time ramp: 0.4-2.0 seconds, linear shape; forward voltage: 180 V; reverse voltage: 120 V) (FIG. 2).

FIG. 2 is a pulsed field gel electrophoresis (PFGE) photograph of the genomic DNA of the bacteriophage ΦCJ19, and it may be confirmed that the genomic DNA of the bacteriophage ΦCJ19 has a size of about 54 kb. In FIG. 2, M is a protein that becomes a standard for measuring a molecular weight.

Example 5

Protein Pattern Analysis of ΦCJ19

15 μl of purified bacteriophage ΦCJ19 solution at a titer of $10^{10}$ pfu/ml was mixed with 3 μl of a 5×SDS sample solution, and heated for 5 minutes. Then, 12% SDS-PAGE was performed (FIG. 3).

Figure 3:
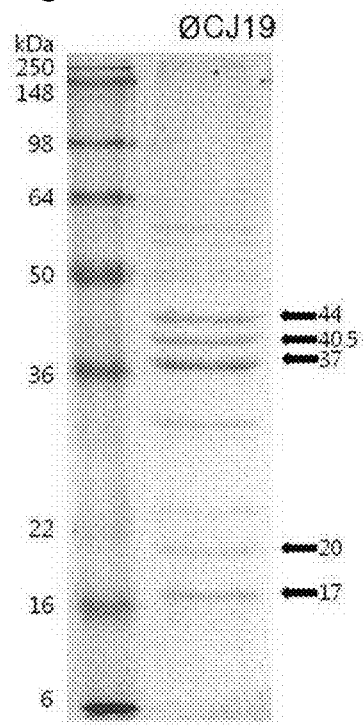
FIG. 3 shows a sodiumdodecylsulfate-polyacrylamide gel electrophoresis (SDS-PAGE) result of the novel bacteriophage ΦCJ19.

FIG. 3 is an electrophoresis photograph showing a result of SDS-PAGE performed on the bacteriophage ΦCJ19, and main proteins having sizes of about 44 kDa, 40.5 kDa, 37 kDa, 20 kDa, and 17 kDa were observed.

Example 6

Genetic Property Analysis of ΦCJ19

In order to confirm genetic characteristics of the bacteriophage ΦCJ19 purified in Example 1, DNA of the bacteriophage ΦCJ19 was analyzed using a FLX titanium sequencer (Roche), which is a gene analysis apparatus. Genes was assembled at Macrogen INC. using GS and de novo assembler software (Roche). Sequence analysis of an open reading frame was performed using GeneMArk.hmm, Glimmer v3.02, and FGENESB software. Identification of the open reading frame was performed using BLASTP and InterProScan program.

The genome sequence of the bacteriophage had various similarities with that of the existing reported bacteriophage, but it was confirmed that a bacteriophage of which all of the fractions were completely (100%) equal to those of the bacteriophage of the present invention did not exist. Therefore, it may be confirmed that the bacteriophage was a newly isolated bacteriophage.

The following Table 2 shows results obtained by comparing homologues of the genome sequence of the bacteriophage ΦCJ19 and decoded genome sequences of other bacteriophages.

Table 2

| Name | Query Length | Start | End | Subject Description | Score E-Value | Identities Match/Total | Pct. (%) |
|---|---|---|---|---|---|---|---|
| contig00001_orf00001 | 159 | 1 | 144 | hypothetical protein [Enterobacteria phage F20] | 8E-16 | 41/48 | 85 |
| contig00001_orf00009 | 294 | 4 | 282 | TfmS [Enterobacteria phage TLS] | 2E-32 | 67/93 | 72 |
| contig00001_orf00018 | 231 | 1 | 228 | gp32 [Escherichia phage phiEB49] | 8E-37 | 73/76 | 96 |

Table 2-continued

| Name | Length | Start | End | Description | E-Value | Match/Total | Pct. (%) |
|---|---|---|---|---|---|---|---|
| contig00001_orf00013 | 726 | 1 | 717 | gp48 [Enterobacteria phage TLS] | 2E-109 | 179/240 | 74 |
| contig00001_orf00014 | 594 | 4 | 591 | putative tail assembly protein [Enterobacteria phage T1] | 2E-76 | 157/196 | 80 |
| contig00001_orf00017 | 918 | 1 | 915 | gp33 [Escherichia phage phiEB49] | 1E-162 | 284/305 | 93 |
| contig00001_orf00012 | 747 | 13 | 744 | thmL [Enterobacteria phage TLS] | 1E-108 | 188/244 | 77 |
| contig00001_orf00030 | 729 | 7 | 726 | hypothetical protein [Enterobacteria phage F20] | 8E-90 | 170/241 | 70 |
| contig00001_orf00043 | 375 | 1 | 330 | JK_56P [Enterobacteria phage JK06] | 3E-44 | 80/110 | 72 |
| contig00001_orf00026 | 474 | 1 | 426 | gp22 [Escherichia phage phiEB49] | 3E-72 | 129/142 | 90 |
| contig00001_orf00024 | 1920 | 1 | 423 | putative tail fiber [Enterobacteria phage RTP] | 7E-55 | 127/141 | 90 |
| contig00001_orf00036 | 1143 | 1 | 1134 | hypothetical protein Shfl1p67 [Shigella phage Shfl1] | 1E-170 | 290/380 | 76 |
| contig00001_orf00037 | 174 | 1 | 171 | gp10 [Escherichia phage phiEB49] | 1E-23 | 52/57 | 91 |
| contig00001_orf00044 | 1584 | 1 | 1581 | conserved protein [Enterobacteria phage RTP] | 0 | 485/527 | 92 |
| contig00001_orf00025 | 924 | 1 | 918 | putative DNA primase [Enterobacteria phage RTP] | 1E-162 | 275/306 | 89 |
| contig00001_orf00046 | 351 | 4 | 348 | hypothetical protein [Enterobacterla phage RTP] | 6E-51 | 94/115 | 81 |
| contig00001_orr00075 | 546 | 1 | 537 | putative polynucleotlde kinase/phosphatase [Enterobacteria phage RTP] | 3E-76 | 137/179 | 76 |
| contig00001_orf00050 | 240 | 1 | 237 | hypothetical protein [Enterobacteria phage RTP] | 1E-36 | 72/79 | 91 | please see the [partial genome Sequence of ΦCJ19] in attachment.

Example 7

Stability Test of ΦCJ19 Depending on pH

In order to confirm whether or not the bacteriophage ΦCJ19 may have stability in a low pH environment in stomach, stability test was performed over a wide pH range (pH 3.0, 3.5, 4.0, 5.5, 6.4, 7.5, 8.3, 9.2, and 11.0).

For test, various pH solutions (sodium acetate buffer (pH 4.0, pH 5.5, and pH 6.4), sodium citrate buffer (pH 3.0 and pH 3.5), sodium phosphate buffer (pH 6.9 and pH 7.4), and Tris-HCl solution (pH 8.2, pH 9.0, pH 9.8, and pH 11.0)) were prepared at a concentration of 0.2 M, respectively.

After 180 μl of each of the pH solutions was mixed with 20 μl of bacteriophage solution having a titer of $5.0 \times 10^{10}$ pfu/ml so that a concentration of each of pH solution became 1 M, and each of the pH solutions was left at room temperature for 2 hours. In a control group, 20 μl of the bacteriophage solution ($5.0 \times 10^{10}$ pfu/ml) was mixed with 180 μl of SM solution and then left at room temperature for 2 hours. Then, the reaction solution was diluted step by step, 10 μl of the diluted solution at each step was dropped and cultured at 30° C. for 18 hours by a soft agar overlay method, and the titer was measured through the presence or absence of lysis (FIG. 4).

Figure 4:
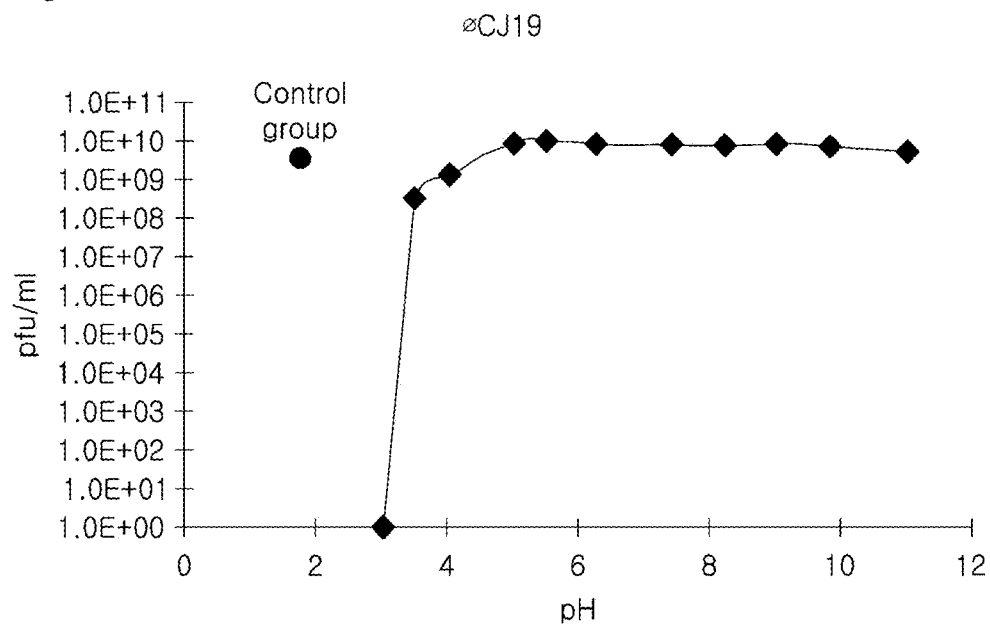
FIG. 4 is a graph showing a result of an acid resistance test of the novel bacteriophage ΦCJ19.

FIG. 4 shows a result of the acid resistance test of the bacteriophage ΦCJ19. As shown in FIG. 4, it may be confirmed that the bacteriophage ΦCJ19 did not lose its activity and was stable in a pH range of 4.0 to 11.0 as compared to the control group.

Example 8

Stability Test of ΦCJ19 Depending on Temperature

A test for confirming stability against heat generated during a formulating process of the bacteriophage in the case of using the bacteriophage as a feed additive formulation among formulations of the bacteriophage was performed.

In detail, 100 μl of bacteriophage ΦCJ19 solution having a concentration of $5.0 \times 10^{10}$ pfu/ml was left at 37° C., 42° C., 53° C., and 60° C. for 0, 30, 60, and 120 minutes, respectively. Then, the solutions above were diluted step by step, 10 μl of each of the diluted solutions was dropped and cultured at 30° C. for 18 hours by a soft agar overlay method, and the titer was measured through the presence or absence of lysis (FIG. 5).

Figure 5:
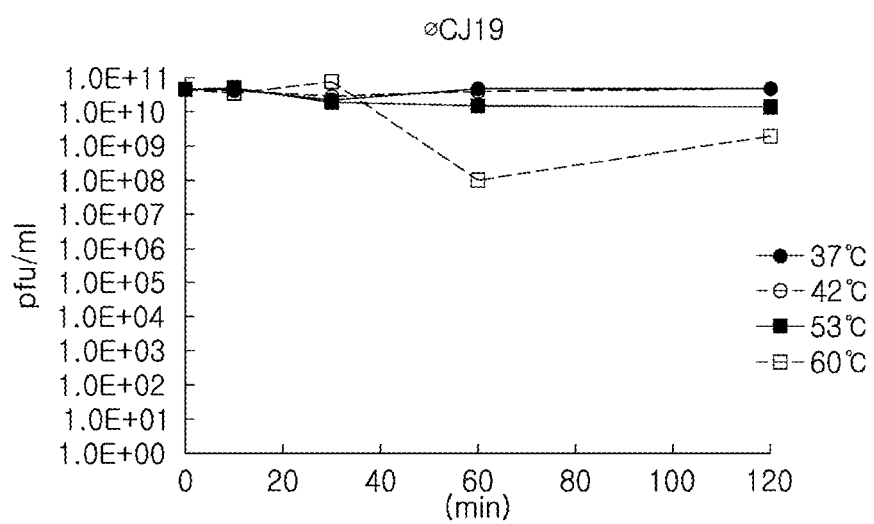
FIG. 5 is a graph showing a result of a heat resistance test of the novel bacteriophage ΦCJ19.

FIG. 5 shows a result of a heat resistance test of the bacteriophage ΦCJ19. As shown in FIG. 5, the bacteriophage ΦCJ19 maintained its activity even though exposed at 53° C. for up to 2 hours, but its activity was reduced according to the exposure time, after exposed at 60° C. for 60 minutes.

Example 9

Infection Spectrum Test of ΦCJ19 on Wild-Type Strains of ETEC

Whether or not the bacteriophage ΦCJ19 had a lytic activity was tested on 15 wild-type strains of ETEC obtained from College of Veterinary Medicine, Seoul National University and University of Guelph in Canada other than ETEC (SNUJG280) used in the experiment.

In detail, 10 μl of bacteriophage ΦCJ19 solution having a titer of $10^9$ pfu/ml and mixed with 150 μl of a shake culture solution ($OD_{600}$=2) of each of the strains was dropped and cultured at 30° C. for 18 hours by a soft agar overlay method. Then, whether or not a plaque was formed was observed.

The results were shown in the following Table 3.

TABLE 3

| Serotype | Strain | Plaque formation |
|---|---|---|
| ETEC | SNU345 | x |
|  | SNU105 | x |
|  | SNU0122 | o |
|  | SNU0149 | o |
|  | SNUJG280 | o |
|  | SNUF4 | o |
|  | SNU162 | o |
|  | SNU160 | o |
|  | SNU107 | o |
|  | CANR08 | o |
|  | SNU2618 | o |
|  | SNU2617 | x |
|  | SNU193 | x |
|  | SNU274 | o |
|  | SNU3220 | o |

As shown in Table 3, the bacteriophage showed infectivity on F-serotype K88 (SNU107, SNU160, SNU162, SNUF4, SNU3220, CANR08, SNUJG280) and K99 (SNU2618) as well as ETEC 0-serotype 0149 (SNU107, SNUF4, SNUJG280, SNU3220, and CANR08) which is the most common cause of diarrhea in swine. Therefore, it may be expected that the bacteriophage will show excellent efficiency at the time of actually applying the bacteriophage.

The invention claimed is:

1. A method of preparing an animal feed composition, the method comprising:
   providing a bacteriophage composition comprising a bacteriophage having the nucleic acid sequence of SEQ ID No: 1; and
   mixing the composition with an animal feed base to provide the animal feed composition such that the bacteriophage is in an amount of $1\times10^6$ to $5\times10^{12}$ PFU/ml with reference to the total amount of the animal feed composition.

2. The method of claim 1, further comprising:
   mixing, with the animal feed base, one or more additives selected from the group consisting of an amino acid, a vitamin, an enzyme, a probiotic, a flavoring agent, a non-protein nitrogen compound, a silicate, a buffer, a coloring agent, an extractant and an oligosaccharide.

3. A method of feeding, the method comprising:
   preparing the animal feed composition according to the method of claim 1; and
   feeding, to an animal, the animal feed composition as a feed.

4. A method of preparing a drinking water composition, the method comprising:
   providing a bacteriophage composition comprising a bacteriophage having the nucleic acid sequence of SEQ ID No: 1; and
   mixing the composition with drinking water to provide the drinking water composition such that the bacteriophage is in an amount of $1\times10^6$ to $5\times10^{12}$ PFU/ml with reference to the total amount of the drinking water composition.

5. The method of claim 4, further comprising:
   mixing, with the animal feed base, one or more additives selected from the group consisting of an amino acid, a vitamin, an enzyme, a probiotic, a flavoring agent, a non-protein nitrogen compound, a silicate, a buffer, a coloring agent, an extractant and an oligosaccharide.

6. A method of feeding, the method comprising:
   preparing the drinking water composition according to the method of claim 4; and
   feeding, to an animal, the drinking water composition as drinking water.

7. A method of treating an infectious disease caused by ETEC, the method comprising:
   administering a bacteriophage composition to a subject in need of such treatment, wherein the bacteriophage composition comprises a pharmaceutically acceptable carrier and a bacteriophage having the nucleic acid sequence of SEQ ID No: 1 in an amount of $1\times10^6$ to $5\times10^{12}$ PFU/ml with reference to the total amount of the bacteriophage composition.

8. A method of claim 7, wherein the infectious disease is colibacillosis.

9. A method of retarding progress of an infectious disease caused by ETEC, the method comprising:
   feeding an animal feed composition to an animal, wherein the animal feed composition comprising an animal feed base and a bacteriophage having the nucleic acid sequence of SEQ ID No: 1 in an amount of $1\times10^6$ to $5\times10^{12}$ PFU/ml with reference to the total amount of the animal feed composition.

10. A method of claim 9, wherein the infectious disease is colibacillosis.

* * * * *

UNITED STATES PATENT AND TRADEMARK OFFICE
CERTIFICATE OF CORRECTION

PATENT NO. : 9,657,277 B2
APPLICATION NO. : 14/770429
DATED : May 23, 2017
INVENTOR(S) : Eun Mi Shin Page 1 of 2

It is certified that error appears in the above-identified patent and that said Letters Patent is hereby corrected as shown below:

On the Title Page

In the right column, at the 18th line after Other Publications, change "Bactenophages" to --Bacteriophages--.

In the Specification

In Column 1 at Line 4, above "TECHNICAL FIELD" insert the following:
--CROSS REFERENCE TO RELATED APPLICATIONS
This application is the U.S. National Phase Application under 35 U.S.C. §371 of
International Application No. PCT/KR2014/001477, filed Feb. 24, 2014, designating the
U.S. and published as WO 2014/133290 A1 on Sep. 4, 2014 which claims the benefit of
Korean Patent Application No. KR-10-2013-0021497, filed Feb. 27, 2013. Any and all
applications for which a foreign and/or a domestic priority is claimed is/are identified in the
Application Data Sheet filed herewith and is/are hereby incorporated by reference in their
entirety under 37 C.F.R. §1.57.
REFERENCE TO SEQUENCE LISTING
This application incorporates by reference the sequence listing submitted as
ASCII text filed via EFS-Web on Aug. 25, 2015, and updated by a file entitled
"AIP22.015APC_REPLACEMENT_SEQLIST.txt" which is 65,025 bytes in size, created
on Nov. 19, 2015, and last modified on Nov. 25, 2015.--.

In Column 1 at Line 26, change "*coil*" to --*coli*--.

In Column 1 at Line 27, change "*coil*" to --*coli*--.

Signed and Sealed this
Seventeenth Day of October, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,657,277 B2

In Column 1 at Line 28 (first occurrence), change "*coil*" to --*coli*--.

In Column 1 at Line 28 (second occurrence), change "*coil*" to --*coli*--.

In Column 1 at Line 29, change "enteroinvacive" to --enteroinvasive--.

In Column 1 at Line 29 (first occurrence), change "*coil*" to --*coli*--.

In Column 1 at Line 29 (second occurrence), change "*coil*" to --*coli*--.

In Column 4 at Line 44, change "Seodamun-gu," to --Seodaemun-gu,--.

In Column 9 at Line 14, change "Chungchong" to --Chungcheong--.

In Column 10 at Line 28, change "bacteriocidal" to --bactericidal--.

In Column 10 at Line 31, change "Seodamun-gu," to --Seodaemun-gu--.